(12) United States Patent
Qin et al.

(10) Patent No.: US 11,207,446 B2
(45) Date of Patent: Dec. 28, 2021

(54) DECELLULARIZED PLACENTAL MEMBRANE AND METHODS OF PREPARING AND USE THEREOF

(71) Applicant: LifeNet Health, Virginia Beach, VA (US)

(72) Inventors: Xiaofei Qin, Virginia Beach, VA (US); Silvia Chen, Hillsborough, NJ (US); Lindsey Aschenbach, Austin, TX (US); Jingsong Chen, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 150 days.

(21) Appl. No.: 16/063,357

(22) PCT Filed: Dec. 23, 2016

(86) PCT No.: PCT/US2016/068526
§ 371 (c)(1),
(2) Date: Jun. 18, 2018

(87) PCT Pub. No.: WO2017/112934
PCT Pub. Date: Jun. 29, 2017

(65) Prior Publication Data
US 2018/0361026 A1 Dec. 20, 2018

Related U.S. Application Data

(60) Provisional application No. 62/387,155, filed on Dec. 23, 2015.

(51) Int. Cl.
| | | |
|---|---|---|
| *A61L 27/36* | (2006.01) | |
| *A61L 27/60* | (2006.01) | |
| *A61L 27/54* | (2006.01) | |
| *A61L 27/38* | (2006.01) | |
| *A61K 35/50* | (2015.01) | |
| *C12N 5/071* | (2010.01) | |
| *C12N 5/074* | (2010.01) | |

(52) U.S. Cl.
CPC .......... *A61L 27/3687* (2013.01); *A61K 35/50* (2013.01); *A61L 27/3604* (2013.01); *A61L 27/3633* (2013.01); *A61L 27/3683* (2013.01); *A61L 27/3691* (2013.01); *A61L 27/3834* (2013.01); *A61L 27/54* (2013.01); *A61L 27/60* (2013.01); *C12N 5/0607* (2013.01); *C12N 5/0691* (2013.01); *A61L 2300/414* (2013.01); *A61L 2430/10* (2013.01); *A61L 2430/34* (2013.01); *A61L 2430/40* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,916,266 A | 6/1999 | Yui et al. | |
| 6,152,142 A | 11/2000 | Tseng | |
| 6,326,019 B1 | 12/2001 | Tseng | |
| 6,734,018 B2 | 5/2004 | Wolfinbarger, Jr. et al. | |
| 6,743,574 B1 | 6/2004 | Wolfinbarger, Jr. et al. | |
| 7,338,757 B2 | 3/2008 | Wolfinbarger, Jr. et al. | |
| 8,357,403 B2 | 1/2013 | Daniel et al. | |
| 8,372,437 B2 | 2/2013 | Daniel | |
| 8,563,232 B2 | 10/2013 | Wolfinbarger, Jr. et al. | |
| 8,574,826 B2 | 11/2013 | Wolfinbarger, Jr. et al. | |
| 2003/0187515 A1 | 10/2003 | Hariri et al. | |
| 2004/0048796 A1* | 3/2004 | Hariri ................... A61K 35/50 424/423 |
| 2008/0044848 A1 | 2/2008 | Heidaran | |
| 2011/0206776 A1 | 8/2011 | Tom et al. | |
| 2013/0084314 A1 | 4/2013 | Horton et al. | |
| 2014/0065238 A1 | 3/2014 | Wolfinbarger, Jr. et al. | |
| 2014/0154663 A1 | 6/2014 | Wolfinbarger, Jr. et al. | |
| 2014/0212390 A1 | 7/2014 | Tabet, Jr. et al. | |

FOREIGN PATENT DOCUMENTS

| | | | | |
|---|---|---|---|---|
| WO | WO 07/010305 | * | 1/2007 | |
| WO | 2013095830 A1 | | 6/2013 | |
| WO | WO 2016/196313 A1 | | 12/2016 | |
| WO | WO 17/049215 | * | 3/2017 | ............. A61L 27/60 |

OTHER PUBLICATIONS

Flynn et al, J Biomed Mater Res, 2006, 79A: 359-369. (Year: 2006).*
Lim JJ, Koob TJ. Placental Cells and Tissues: the transformative rise in advanced wound care. In: Fonseca C, editor. Worldwide wound healing—innovation in natural and conventional methods. Rijeka: InTech; 2016. p. 121-151. https://doi.org/10.5772/65321. (Year: 2016).*
Crapo et al, Biomaterials, 2011, 32: 3233-3243. (Year: 2011).*
Keane et al, Methods, 2015, 84:25-34. (Year: 2015).*
International Preliminary Report on Patentability for International Application No. PCT/US2016/068526, dated Jun. 26, 2018, 14 pages.
Choi et al., Tissue Engineering: Part A, 19(3/4):329-39 (2013).
Hunt, Transfus Med Hemother, 38:107-23 (2011).
International Search Report for PCT International Application No. PCT/US2016/068526 dated Mar. 17, 2017.

(Continued)

*Primary Examiner* — Allison M Fox
(74) *Attorney, Agent, or Firm* — RatnerPrestia

(57) ABSTRACT

A method of preparing a decellularized placental membrane is provided. The method comprises removing cells from a pre-decellularized placental membrane comprising an amnion layer and a chorion layer to produce a decellularized placental membrane without separating the amnion layer from the chorion layer. The pre-decellularized placental membrane is obtained from an amniotic sac, and the decellularized placental membrane comprises the amnion layer and the chorion layer. Also provided is a decellularized placental membrane and a placenta-derived graft comprising the decellularized placental membrane. Further provided are the uses of the decellularized placental membrane or the placenta-derived graft.

18 Claims, 8 Drawing Sheets

(56) References Cited

OTHER PUBLICATIONS

Koob et al., J Biomed Mater Res Part B, pp. 1-10 (2014).
Extended European Search Report for European Application No. 16880147.0, dated Jul. 25, 2019, 9 pages.
Jauniaux et al., "Fluid Compartments of the Embryonic Environment". Human Reproduction Update 2000. vol. 6 (3):268-278.
Schmidt, "The Amniotic Fluid Compartment: The Fetal Habitat", Adv. Anat. Embryol Coll Biol., 1992; 127:1-100, abstract only.
European Communication pursuant to Article 94(3) for European Application No. 16 880 147.0, dated Jul. 10, 2020, 7 pages.
Abshier, "A Closer look At The Potential of Placental Membrane Grafts For Chronic Diabetic Foot Ulcerations", Podiatry Today, 2015 , vol. 28(11) pp. 20-26.
Indian Examination Report for Indian Application No. 201817026541, dated Aug. 20, 2021, with English translation, 6 pages.

\* cited by examiner

A. B.

A. B.

ived placenta graft comprising the decellularized
DECELLULARIZED PLACENTAL MEMBRANE AND METHODS OF PREPARING AND USE THEREOF

CROSS-REFERENCE TO RELATED APPLICATION

This application is a U.S. national phase application of International Application No. PCT/US2016/068526, filed Dec. 23, 2016 claiming the benefit of U.S. Provisional Application No. 62/387,155 filed Dec. 23, 2015, the contents of each of which are incorporated herein by their entireties for all purposes.

BACKGROUND OF THE INVENTION

The invention relates to a decellularized placental membrane, methods of preparing the decellularized placental membrane from an amniotic sac, and methods of use thereof.

SUMMARY OF THE INVENTION

The invention relates to a decellularized placental membrane comprising amnion and chorion layers and methods of preparing of using thereof.

A method of preparing a decellularized placental membrane is provided. The method comprises removing cells from a pre-decellularized placental membrane comprising an amnion layer and a chorion layer to produce a decellularized placental membrane without separating the amnion layer from the chorion layer. The pre-decellularized placental membrane is obtained from an amniotic sac, and the decellularized placental membrane comprises the amnion layer and the chorion layer.

In accordance with the preparation method, the decellularized placental membrane may comprise one or more growth factors in an amount that is at least 10% greater than the sum of the amount of the one or more growth factors in a decellularized control isolated amniotic membrane and the amount of the one or more growth factors in a decellularized control isolated chorionic membrane having a substantially identical area size; the decellularized placental membrane may comprise one or more growth factors in an amount that is at least 20% of the amount of the one or more growth factors in the pre-decellularized placental membrane; the decellularized placental membrane may comprise less than 100 ng dsDNA per mg dry weight of the decellularized placental membrane; or the decellularized placental membrane may comprise DNA in an amount that is less than 10% of the DNA in the pre-decellularized placental membrane.

In accordance with the preparation method, the amnion layer in the decellularized placental membrane may comprise a fibroblast layer and the chorion layer in the decellularized placental membrane may comprise a reticular layer; or the amnion layer in the decellularized placental membrane may comprise epithelium, a basement membrane, a compact layer, a fibroblast layer, and a spongy layer, while the chorion layer in the decellularized placental membrane may comprise a cellular layer, a reticular layer, a pseudo-basement membrane, and a trophoblast layer.

The preparation method may further comprise harvesting the amniotic sac from a donor.

The preparation method may further comprise cleaning and disinfecting the pre-decellularized placental membrane.

The preparation method may further comprise treating the pre-decellularized placental membrane with a reagent comprising one or more denaturing detergents.

The preparation method may further comprise treating the pre-decellularized placental membrane with a reagent comprising one or more non-denaturing detergents.

The preparation method may further comprise freezing or freeze-drying the decellularized placental membrane.

The preparation method may further comprise sterilizing the decellularized placental membrane.

The preparation method may further comprise storing the decellularized placental membrane at room temperature, temperature of 10° C. or below, freezing, or in cryopreservation. The stored decellularized placental membrane may have a water content of less than 0.5% by weight based on the total weight of the decellularized placental membrane. The stored decellularized placental membrane may have a water content of 5-95% by weight based on the total weight of the decellularized placental membrane.

The preparation method may further comprise treating the decellularized placental membrane with a water replacing agent. The water replacing agent may comprise one or more agents selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids.

The preparation method may further comprise immobilizing the pre-decellularized placental membrane on a substrate before removing the cells such that the decellularized placental membrane is immobilized on the substrate, and storing the immobilized decellularized placental membrane. The preparation method may further comprise freezing or freeze-drying the immobilized decellularized placental membrane.

A decellularized placental membrane prepared by the preparation method is also provided.

A decellularized placental membrane comprising an amnion layer and a chorion layer is further provided. The amnion layer and the chorion layer are derived from a placental membrane without separation of the amnion layer from the chorion layer.

The decellularized placental membrane of the present invention may comprise one or more growth factors in an amount that is at least 10% greater than the sum of the amount of the one or more growth factors in a decellularized control isolated amniotic membrane and the amount of the one or more growth factors in a decellularized control isolated chorionic membrane have a substantially identical area size; the decellularized placental membrane may comprise one or more growth factors in an amount that is at least 20% of the amount of the one or more growth factors in the pre-decellularized placental membrane; the decellularized placental membrane may comprise platelet-derived growth factor (PDGF) in an amount that is at least 20% of the amount of the PDGF in the pre-decellularized placental membrane; the decellularized placental membrane may comprise basic fibroblast growth factor (bFGF) in an amount that is at least 20% of the amount of the bFGF in the pre-decellularized placental membrane; or the decellularized placental membrane may comprise DNA in an amount that is less than 20% of the DNA in the pre-decellularized placental membrane.

A placenta-derived graft comprising the decellularized placental membrane of the present invention and one or more agents is provided. The one or more agents may be selected from the group consisting of preservatives, water replacing agents, other soft tissue, synthetic materials, and combinations thereof.

A method comprising culturing cells in the presence of the decellularized placental membrane or the placenta-derived graft of the present invention is provided. The cells may be selected from the group consisting of stem cells, adipose derived stem cells, dorsal root ganglion cells, pancreatic islet cells, cardiomyocytes, hepatocytes, iPSCs, cancer cells, and umbilical vein endothelial cells. The culturing method may further comprise storing the cultured cells in the presence of the decellularized placental membrane or the placenta-derived graft. The cells may be stored by cryopreservation.

A method of promoting differentiation of pluripotent stem cells or tissue-specific progenitor cells is provided. The method comprises culturing the pluripotent stem cells or tissue-specific progenitor cells in the presence of an effective amount of the decellularized placental membrane or the placenta-derived graft of the present invention.

A method of repairing a defect in a tissue is provided. The method comprises contacting the site of defect with an effective amount of the decellularized placental membrane or the placenta-derived graft of the present invention.

DETAILED DESCRIPTION OF THE INVENTION

Figure 1:
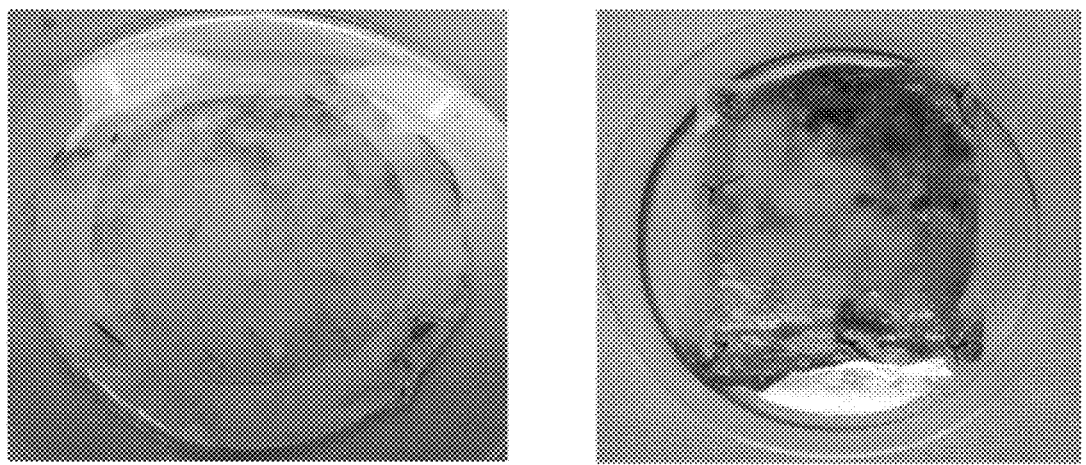
FIG. 1 depicts exemplary pre-decellularized placental membranes sutured on two different shaped frames without cleaning and cell removal.

The invention relates to a method of preparing a decellularized placental membrane from a pre-decellularized placental membrane comprising an amnion layer and a chorion layer by removing cells without separating the amnion layer and the chorion layer. The decellularized placental membrane may be used for preparing placenta-derived grafts, culturing cells, promoting differentiation and/or increasing maintenance of self-renewing ability of pluripotent stem cells or tissue-specific progenitor cells, and repairing a defect in a tissue.

The term "amniotic sac" as used herein refers to a thin but tough placental membrane that holds amniotic fluid in which an embryo and later a fetus develops. The amniotic sac comprises an inner layer (i.e., an amnion layer) and an outer layer (i.e., a chorion layer). The amnion layer comprises several sub-layers, for example, epithelium, a basement membrane, a compact layer, a fibroblast layer, and a spongy layer (from inside to outside). Similarly, the chorion layer comprises several sub-layers, for example, a cellular layer, a reticular layer, a pseudo-basement membrane, and a trophoblast layer (from inside to outside). The amnion layer and the chorion layer each comprise cells as well as cellular and extracellular molecules (e.g., growth factors, enzymes, and extracellular matrix molecules). The amniotic sac may be obtained from a donor. The donor may be a mammal, for example, human, bovine, porcine, murine, ovine, equine, canine, caprine and feline, preferably a human.

The term "pre-decellularized placental membrane" used herein refers to a piece of membrane of an amniotic sac. The pre-decellularized placental membrane may be a whole, complete, or a part of a placental membrane having the amnion layer and the chorion layer in the amniotic sac. The pre-decellularized placental membrane may be obtained from the amniotic sac by any method and may be of any size or shape. The amnion layer in the pre-decellularized placental membrane may comprise several sub-layers, for example, epithelium, a basement membrane, a compact layer, a fibroblast layer and a spongy layer (from inside to outside). The amnion layer in the pre-decellularized placental membrane may comprise at least the fibroblast layer. The chorion layer in the pre-decellularized placental membrane may comprise several sub-layers, for example, a cellular layer, a reticular layer, a pseudo-basement membrane and a trophoblast layer (from inside to outside). The chorion layer in the pre-decellularized placental membrane may comprise at least the reticular layer. The amnion layer and the chorion layer in the pre-decellularized placental membrane each comprise cells as well as cellular and extracellular molecules (e.g., growth factors, enzymes, and extracellular matrix molecules).

The term "decellularized placental membrane" as used herein refers to a placental membrane obtained by removing a substantial amount, for example, at least about 70, 80, 90, 95, 99, 99.9 or 99.999% of the cells from a pre-decellularized placental membrane. The decellularized placental membrane of the present invention comprises the amnion layer and the chorion layer in the pre-decellularized placental membrane. The amnion placental membrane may comprise epithelium, a basement membrane, a compact layer, a fibroblast layer and/or a spongy layer while the chorion the decellularized placental membrane may comprise a cellular layer, a reticular layer, a pseudo-basement membrane and/or a trophoblast layer.

The term "isolated amniotic membrane" as used herein refers to a membrane of the amnion layer separated from the chorion layer in the pre-decellularized placental membrane. The separation may be achieved any method. For example, the amnion layer may be peeled or pulled from the chorion layer or detached from the chorion layer by chemical treatment comprising a high salt solution. The isolated amniotic membrane may comprise epithelium, a basement membrane, a compact layer, a fibroblast layer and/or a spongy layer. The isolated amniotic membrane may be decellularized by removing a substantial amount, for example, at least about 70, 80, 90, 95, 99, 99.9 or 99.999% of the cells from the amniotic membrane.

The term "isolated chorionic membrane" as used herein refers to a membrane of the chorion layer separated from the amnion layer in the pre-decellularized placental membrane. The separation may be achieved any method. For example, the chorion layer may be peeled or pulled from the amnion layer or detached from the amnion layer by chemical treatment comprising a high salt solution. The isolated chorionic membrane may comprise a cellular layer, a reticular layer, a pseudo-basement membrane and/or a trophoblast layer. The isolated chorionic membrane may be decellularized by removing a substantial amount, for example, at least about 70, 80, 90, 95, 99, 99.9 or 99.999% of the cells from the chorionic membrane.

The present invention provides a method of preparing a decellularized placental membrane. The method comprises removing cells from a pre-decellularized placental membrane comprising an amnion layer and a chorion layer to produce a decellularized placental membrane without separating the amnion layer from the chorion layer. The pre-decellularized placental membrane is obtained from an amniotic sac. The decellularized placental membrane comprises the amnion layer and the chorion layer.

The term "without separation" as used herein refers to that the amnion layer and the chorion layer remain in contact with each other with a contact surface of, for example, at least about 1, 10, 100, 1,000 or 10,000 mm$^2$ during the step of removing cells from a pre-decellularized placental membrane to produce a decellularized placental membrane. The contact surface between the amnion layer and the chorion layer may overlap with at least about 5, 10, 15, 20, 25, 30, 35, 40, 50, 60, 70, 80, 90, 95, 98 or 99% of the surface of the amnion layer facing the chorion layer. The contact surface may overlap with at least about 5, 10, 15, 20, 25, 30, 35, 40, 50, 60, 70, 80, 90, 95, 98 or 99% of the surface of the chorion layer facing the amnion layer.

The cell removal or decellularizing process described herein may be performed in accordance with the methods described in U.S. Pat. Nos. 6,734,018, 7,338,757, 8,574,826, 6,743,574, and 8,563,232, and U.S. Patent Application Publication No. 2014/0065238A1 and 2014/0154663A1, each of which is incorporated by reference herein in its entirety. The decellularizing process may be performed without damage to matrix and/or tissue structure of the placental membrane and may employ sarcosinates and decontaminating agents. In some embodiments, the decellularizing process may or may not include using detergent, endonuclease, and/or protease. The decellularized placental membrane or a placenta-derived graft may include collagens, hyaluronins, elastins, mucopolysaccharides and proteoglycans, among other components. In some embodiments, the decellularized placental membrane or a placenta-derived graft may comprise more than one type of collagen and/or more than one proteins, other than collagen, collagen type I, and/or collagen type IV.

In some embodiments, the decellularized placental membrane comprises less than about 1000, 500, 100, 80, 50 or 10 ng double-stranded DNA (dsDNA) per mg dry weight of the decellularized placental membrane. In other embodiments, the DNA quantity in the decellularized placental membrane is reduced by about 60, 70, 80, 85, 90, 95, 99% or more; about 60, 70, 80, 85, 90, 95, 99, 100% or less; and/or between about 50 and 100%, between about 70 and 100%, between about 90 and 100%, between about 90 and 95% compared to the DNA quantity in the pre-decellularized placental membrane. The decellularized placental membrane may comprise DNA in an amount that is less than about 50, 40, 30, 20, 10, 5 or 1% of the DNA in the pre-decellularized placental membrane.

The decellularized placental membrane may comprise one or more growth factors and/or cytokines (e.g., platelet-derived growth factor (PDGF), basic fibroblast growth factor (bFGF), epidermal growth factor (EGF), granulocyte-colony stimulating factor (GCSF), placenta growth factor (PIGF), fibroblast growth factor (FGF), transforming growth factor (TGF), macrophage inflammatory protein, interleukins, insulin-like growth factor (IGF), and insulin-like growth factor binding protein (IGFBP)) in an amount that is at least about 1, 5, 10, 15, 20, 25 or 30% greater than the sum of the amount of the one or more growth factors in a decellularized control isolated amniotic membrane and the amount of the one or more growth factors in a decellularized control isolated chorionic membrane having a substantially identical area size. The term "substantially identical area size" as used herein refers to an area size, for example, the size of a section area of a decellularized placental membrane, that is less than about 20, 15, 10, 5 or 1% different from a control area size, for example, the area size of a decellularized isolated amniotic or chorionic membrane. The decellularized control isolated amniotic membrane and the decellularized control isolated chorionic membrane may be prepared from the amniotic sac used to prepare the decellularized placental membrane.

The decellularized placental membrane may comprise one or more growth factors and/or cytokines (e.g., platelet-derived growth factor (PDGF), basic fibroblast growth factor (bFGF), epidermal growth factor (EGF), granulocyte-colony stimulating factor (GCSF), placenta growth factor (PIGF), fibroblast growth factor (FGF), transforming growth factor (TGF), macrophage inflammatory protein, interleukins, insulin-like growth factor (IGF), and insulin-like growth factor binding protein (IGFBP)) in an amount that is at least about 1, 5, 10, 15, 20, 25 or 30% of the amount of the one or more growth factors in the pre-decellularized placental membrane.

The preparation method may further comprise harvesting the amniotic sac from a donor. The donor may be a mammal, for example, human, bovine, porcine, murine, ovine, equine, canine, caprine and feline, preferably a human.

The preparation method may further comprise separating the pre-decellularized placental membrane from a placenta by, for example, cutting the amniotic sac from the placenta around the placenta skirt.

The preparation method may comprise cleaning and disinfecting the pre-decellularized placental membrane. The method may also further comprise removing extraneous tissues associated with the pre-decellularized placental membrane. The pre-decellularized placental membrane may be cut and washed with distilled/deionized endotoxin-free water and/or an aqueous solution, such as isotonic saline, among others. In processing, multiple "washes" or "cleaning" may be affected using volumes of aqueous solution that are 2, 5, or 10 times the approximated volume of the tissue being processed, in some embodiments. The use of three such processing steps may affect an approximate 1:100, 1:500 or 1:1000 dilution of associated solubilizable elements rendering the tissue essentially free from such solubilizable elements. The pre-decellularized placental membrane and decellularized placental membrane pieces may have a thickness of about 30, 20, 15, 10, 8, 5, 3, 2, 1, 0.5, 0.1, 0.05 mm or less, in certain embodiments. The pre-decellularized placental membrane and decellularized placental membrane pieces may also have a thickness of about 30, 20, 10, 8, 5, 3, 2, 1, 0.5, 0.1, 0.05 mm or more. In another aspect, the method described herein may also comprise sterilizing the decellularized placental membrane, and/or placenta derived graft. Sterilization may involve the use of ionizing radiation, in some embodiments. In other embodiments, the absorbed dose of ionizing radiation may be between about 1.0 KGy and about 50 KGy, between about 8.0 KGy and about 50 KGy, between about 8.0 KGy and about 25 KGy, or between about 8.0 KGy and about 18 KGy. In some embodiments, the sterilizing step may include placing the packaged tissue repair implants comprising the decellularized placental membrane on dry ice and irradiating the packaged composition. In certain embodiments, sterilization may be performed at a temperature of between about −20° C. and −50° C. The implants of the present invention may be sterilized using gamma irradiation, supercritical carbon dioxide, ethylene oxide, plasma, or electronic-beam.

The preparation methods may further comprise storing the decellularized placental membrane at, for example, a room temperature, at a low temperature or in cryopreservation. The decellularized placental membrane may be stored in a wet or dry state. The stored decellularized placental membrane may have a water content of less than about 0.5% (e.g., about 0.01-5%) or about 5-95% by weight based on the total weight of the decellularized placental membrane. The method may further comprise treating the decellularized placental membrane with a water replacing agent. The water replacing agent may be selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids.

The method may further comprise freezing or freeze-drying the decellularized placental membrane. The decellularized placental membrane may be freeze-dried to a point such that the freeze-dried fragments have an average residual moisture of less than about 10, 5, 4, 3, 2, 1, 0.5, or 0.1 wt %.

The method may further comprise treating the pre-decellularized placental membrane with a reagent comprising one or more detergents. Examples of the detergents include anionic detergent comprising bile acid salts and/or sodium dodecyl sulfate (SDS); cationic detergent comprising cetyl trimethyl-ammonium bromide (CTAB), and non-ionic or zwitterionic detergents comprising BRIJ®, TRITON® and CHAPS.

The method may further comprise treating the pre-decellularized placental membrane with a reagent comprising one or more denaturing detergent. Example of denaturing detergent include sodium dodecyl sulfate (SDS). The method may further comprise treating the pre-decellularized placental membrane with a reagent comprising one or more non-denaturing detergents. Examples of the non-denaturing detergents include N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester.

Figure 6:
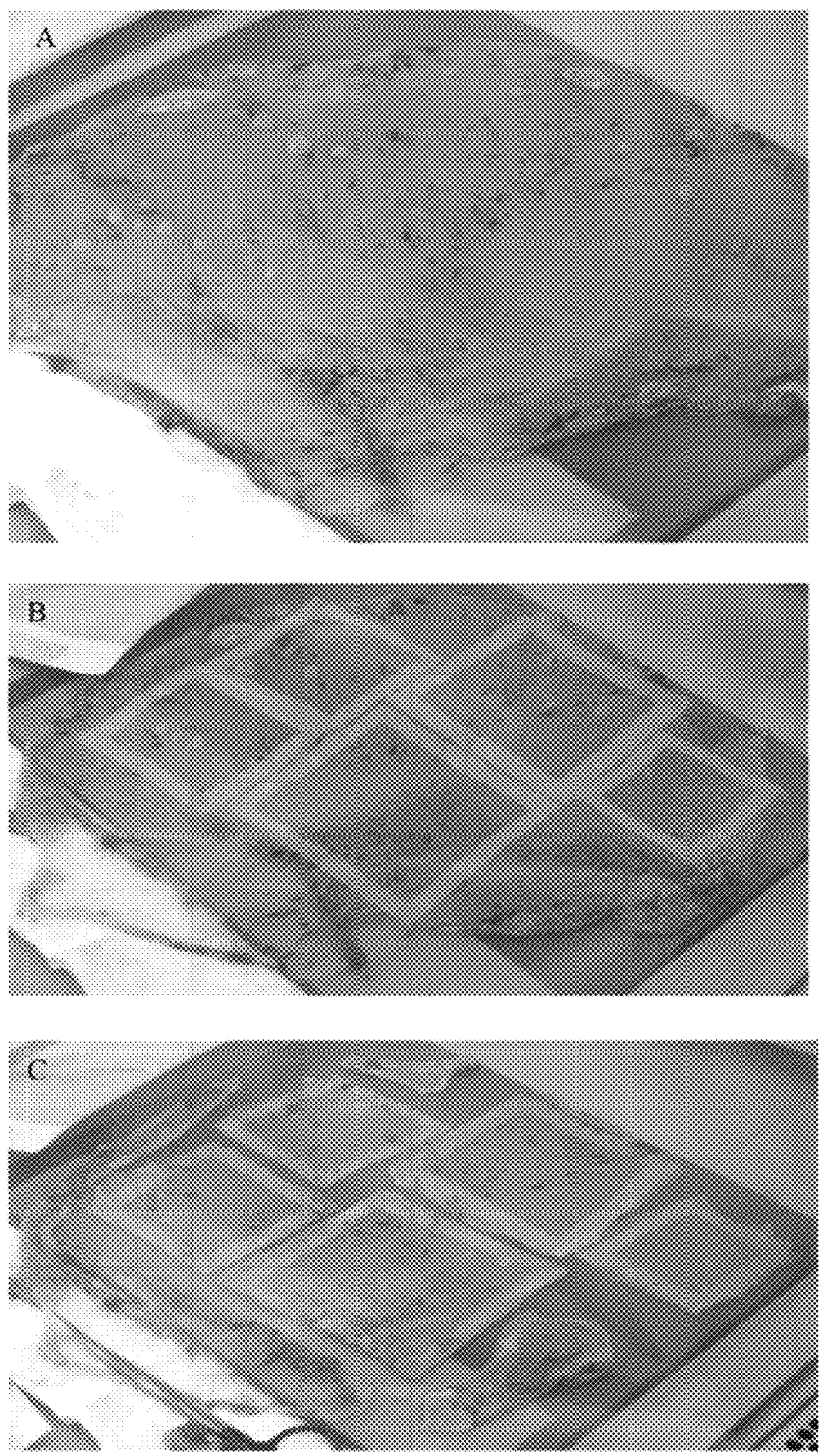
FIG. 6 depicts an exemplary scheme of fixing a pre-decellularized placental membrane on a substrate (A: preparing an exemplary pre-decellularized placental membrane with both amniotic membrane and chorionic membrane; B: laying different sizes of mesh frames on top of the membrane; C: cutting membrane around the matching frames; D: fixing the membrane with the frame with skin staples; and E: washing the pre-decellularized placental membrane piece with frame and staples).
Figure 6:
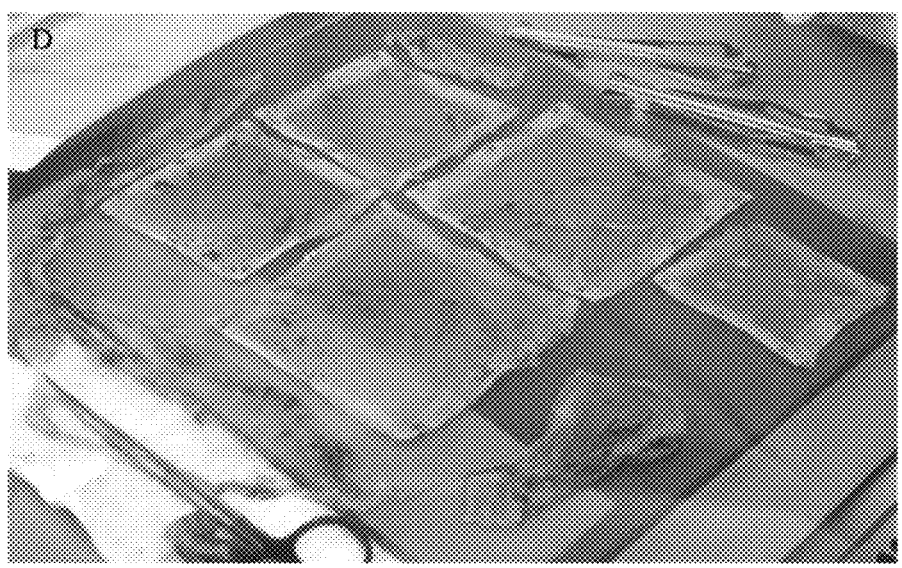
Figure 6:
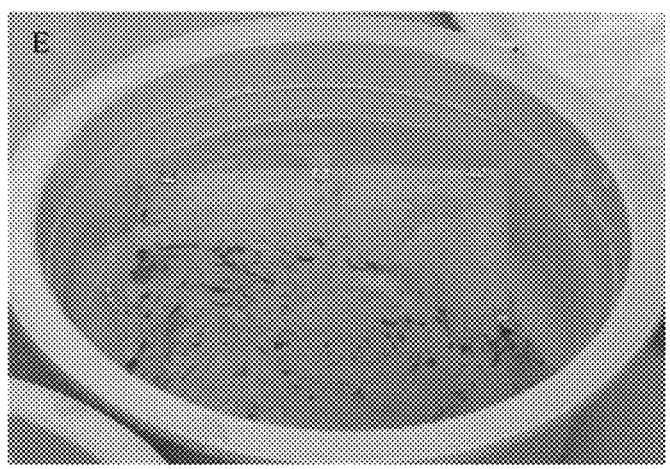
Figure 7:
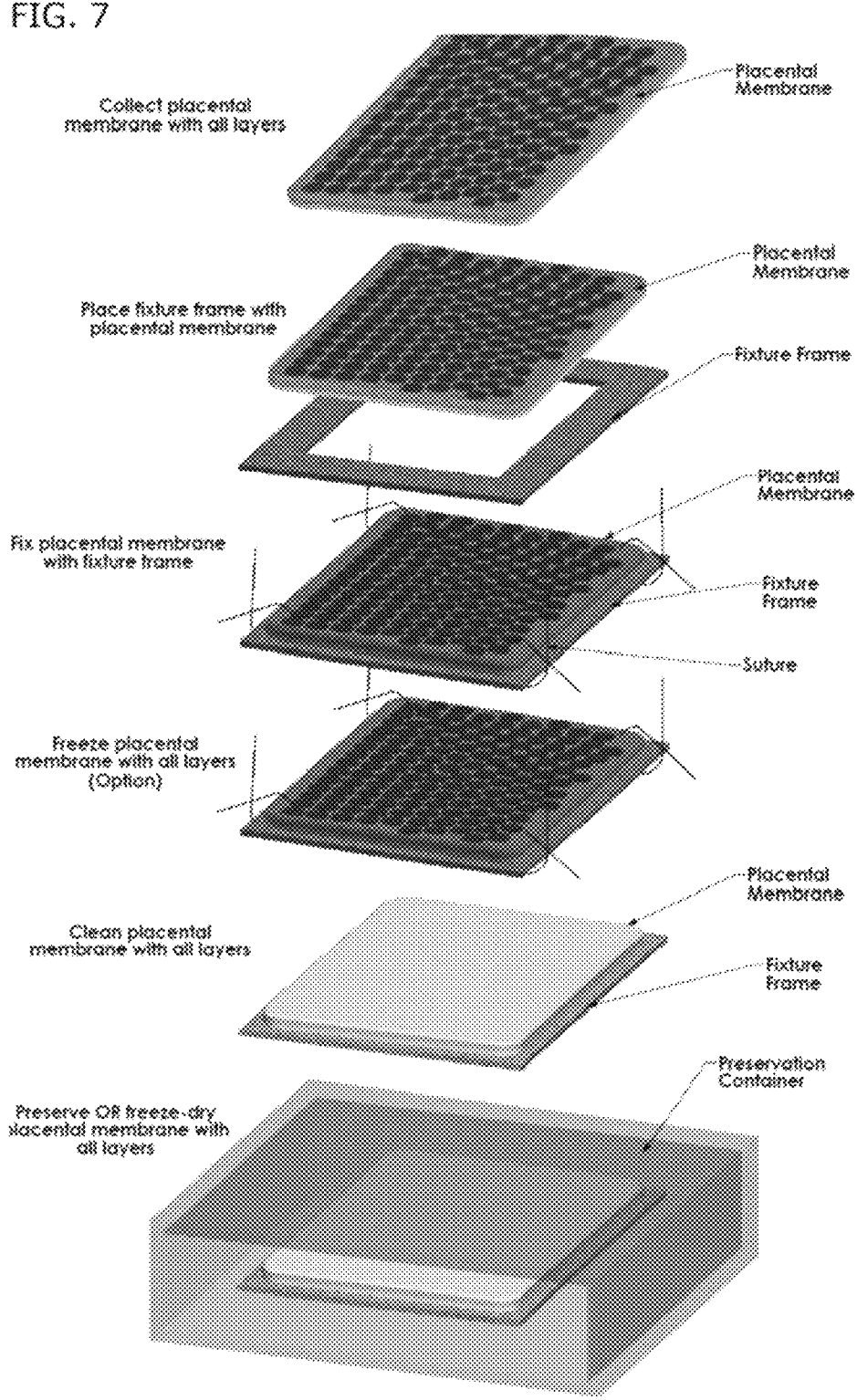
FIG. 7 depicts an exemplary scheme of fixing a pre-decellularized placental membrane on a substrate.
Figure 8:
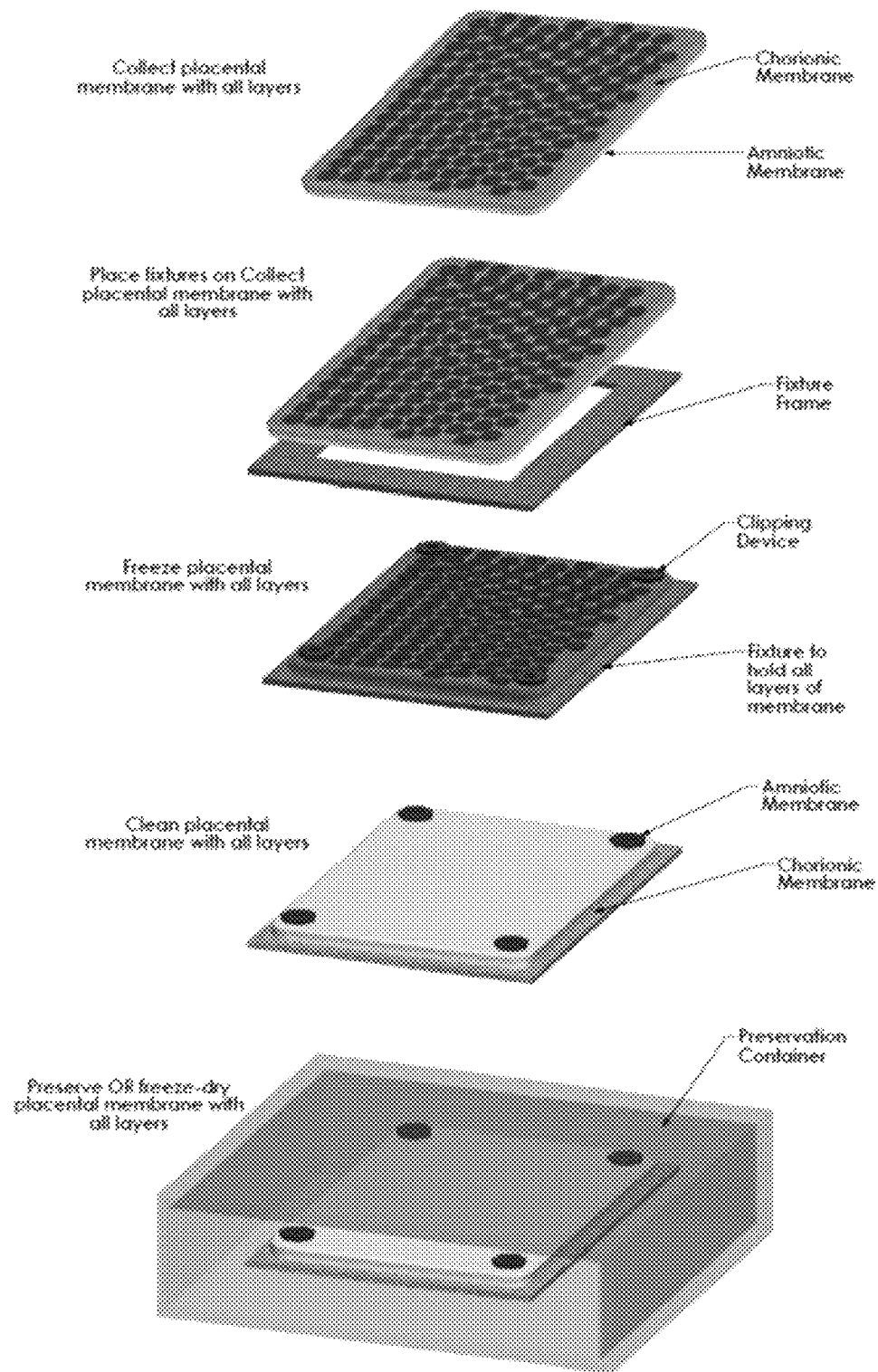
FIG. 8 depicts another exemplary scheme of fixing a pre-decellularized placental membrane on a substrate.

The method may further comprise immobilizing the pre-decellularized placental membrane on a substrate before removing the cells such that the decellularized placental membrane is immobilized on the substrate and storing the immobilized decellularized placental membrane (see FIGS. 6-8). The decellularized placental membrane may be stored on the substrate. The substrate may be made of various components including, but not limited to, polymer, plastic, polypropylene, polyester, metal, and wood. The substrate may be hollow to maximize the surface area of the pre-decellularized placental membrane or the decellularized placental membrane exposed to a liquid (e.g., solution) used for cell removal or storage, respectively. For example, the substrate may be a frame (see FIGS. 6-8). The methods may further comprise freezing, lyophilizing, or freeze-drying the decellularized placental membrane that is immobilized on the substrate.

The method may not include digesting the pre-decellularized placental membrane or decellularized placental membrane in a digestion solution. The digestion solution described herein may include an enzyme to digest at least a part of proteins in the pre-decellularized placenta membrane. For example, the digestion solution may comprise an acid, such as HCl and other strong and weak acids, and a protease including, but not limited to, papain, pepsin, pepsinogen, trypsin, collagenases, and/or dispase. As used herein, the term "and/or" includes any and all combinations of one or more of the associated listed items.

The present invention also provides a decellularized placental membrane prepared according to the preparation method of the present invention.

The present invention also provides a decellularized placental membrane comprising an amnion layer and a chorion layer. The amnion layer and the chorion layer are derived from a placental membrane without separation of the amnion layer from the chorion layer. The amnion layer in the decellularized placental membrane may comprise epithelium, a basement membrane, a compact layer, a fibroblast layer and/or a spongy layer. The chorion layer in the decellularized placental membrane may comprise a cellular layer, a reticular layer, a pseudo-basement membrane and/or a trophoblast layer.

The decellularized placental membrane of the present invention may comprise one or more growth factors and/or cytokines (e.g., platelet-derived growth factor (PDGF), basic fibroblast growth factor (bFGF), epidermal growth factor (EGF), granulocyte-colony stimulating factor (GCSF), placenta growth factor (PlGF), fibroblast growth factor (FGF), transforming growth factor (TGF), macrophage inflammatory protein, interleukins, insulin-like growth factor (IGF), and insulin-like growth factor binding protein (IGFBP)) in an amount that is at least about 1, 5, 10, 15, 20, 25 or 30% greater than the sum of the amount of the one or more growth factors and/or cytokines in a decellularized control isolated amniotic membrane and the amount of the one or more growth factors and/or cytokines in a decellularized control isolated chorionic membrane having substantially identical area size. The term "substantially identical area size" as used herein refers to an area size, for example, the size of a section area of a decellularized placental membrane, that is less than about 20, 15, 10, 5 or 1% different from a control area size, for example, the area size of a decellularized control isolated amniotic or chorionic membrane. The decellularized control isolated amniotic membrane and the decellularized control isolated chorionic membrane may be prepared from the amniotic sac used to prepare the decellularized placental membrane.

The decellularized placental membrane of the present invention may comprise one or more growth factors and/or cytokines (e.g., platelet-derived growth factor (PDGF), basic fibroblast growth factor (bFGF), epidermal growth factor (EGF), granulocyte-colony stimulating factor (GCSF), placenta growth factor (PlGF), fibroblast growth factor (FGF), transforming growth factor (TGF), macrophage inflammatory protein, interleukins, insulin-like growth factor (IGF), and insulin-like growth factor binding protein (IGFBP) in an amount that is at least about 1, 5, 10, 15, 20, 25 or 30% of the amount of the one or more growth factors in the pre-decellularized placental membrane.

The decellularized placental membrane of the present invention may comprise less than about 1000, 500, 100, 80, 50 or 10 ng double-stranded DNA (dsDNA) per mg dry weight of the decellularized placental membrane. The DNA quantity in the decellularized placental membrane may be reduced by about 60, 70, 80, 85, 90, 95, 99% or more; about 60, 70, 80, 85, 90, 95, 99, 100% or less; and/or between about 50 and 100%, between about 70 and 100%, between about 90 and 100%, between about 90 and 95% compared to the DNA quantity in the pre-decellularized placental membrane. The decellularized placental membrane may comprise DNA in an amount that is less than about 50, 40, 30, 20, 10, 5 or 1% of the DNA in the pre-decellularized placental membrane.

The present invention further provides a placenta-derived graft. The placenta-derived graft comprises the decellularized placental membrane of the present invention and one or more agents. The one or more agents may be any agents suitable for graft implantation, and may be selected from the group consisting of preservatives, water replacing agents, other soft tissue, synthetic material, and combinations thereof.

The placenta-derived graft may be an autograft, an allograft, or a xenograft.

As used herein, the term "about" modifying, for example, the dimensions, volumes, quantity of an ingredient in a composition, concentrations, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

In some embodiments, the method further comprises (i) collecting placenta along with the amniotic sac from C-section, (ii) cutting the amniotic sac comprising pre-decellularized placental membrane from placenta, wherein the amnion and chorion layers remain in contact with each other prior to and/or during the decellularization process, and/or (iii) cutting the pre-decellularized placental membrane prior to the decellularization. In additional embodiments, the cutting produced the pre-decellularized placental membrane pieces having an average size of about 1000, 500, 300, 100, 50, 30 or 10 cm$^2$ and/or a dimension of about 0.5, 1, 5, 10, 20, 50, 100, 200, 500 mm or more on average. In further embodiments, the method described herein may also comprise cutting the pre-decellularized placental membrane or the decellularized placental membrane to have a dimension from about 1 mm to about 60 cm, from about 1 mm to about 50 cm, from about 1 cm to about 60 cm, from about 1 cm to about 50 cm, or from about 1 cm to about 10 cm on average. In yet additional embodiments, the method excludes homogenizing the amnion and chorion layers to have an average diameter of less than about 1000, 500, or 100 microns.

In some embodiments, the placenta-derived graft may or may not be a hydrogel. As used herein, the term hydrogel has its art understood meaning and refers to a polymeric matrix that can absorb water to swell and form gels of varying elasticity.

In another aspect, the methods described herein may or may not include adding (i) an additional crosslinking in addition to natural crosslinking from the pre-decellularized placental membrane, (ii) an additional carrier in addition to natural carrier from the pre-decellularized placental membrane, and/or (iii) a photoactive agent to the decellularized placental membrane or the placenta-derived graft. In another aspect, the decellularized placental membrane and/or placenta-derived graft may or may not comprise an additional crosslinker or carrier in addition to a natural crosslinker(s) and a natural carrier(s) from the one or more placental membrane(s).

The pre-decellularized placental membrane described herein may comprise a naturally occurring crosslinker that is configured to create a physical and/or chemical bond at least between two parts (e.g., amnion and chorion layers) of the pre-decellularized placental membrane, for example, before or after harvesting the pre-decellularized placental membrane, freezing, and/or freeze-drying the pre-decellularized placental membrane. The chemical bonds may include ionic, covalent, and/or metallic bonds. For example, natural crosslinkers of the pre-decellularized placenta membrane may be crosslinked to form physical and/or chemical bond by a chemical, physical, and/or temperature treatment prior to or after decellularization. In some embodiments, the methods described herein do not include crosslinking the decellularized placental membrane and/or placenta-derived graft by non-naturally occurring bonds using non-naturally occurring crosslinkers.

In some embodiments, the decellularized placental membrane and/or placenta-derived graft described herein may exclude a non-naturally occurring crosslinker, also called as crosslinking agent herein. In additional embodiments, the decellularized placental membrane described herein does not comprise a non-naturally occurring crosslinker. For example, the decellularized placental membrane and/or placenta-derived graft described herein may exclude a non-naturally occurring crosslinker selected from the group consisting of propylene glycol alginate, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC), dimethyl suberimidate (DMS), dimethyl-3-3'-dithiobispropionimidate (DTBP), acryl azide, and a combination thereof. In additional embodiments, the placenta-derived graft described herein may exclude a photoactive agent selected from the group consisting of a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide-N,N9-bis(3-diazopyruvoyl)-2,29-(ethylenedioxy)bis-(ethylamine) (DPD), diazopyruvoyl (DAP), methylene blue, erythrosin, phloxime, thionine, methylene green, rose Bengal, acridine orange, xanthine dye, thioxanthine dye, ethyl eosin, eosin Y, and a combination thereof.

In another aspect, the pre-decellularized placental membrane described herein may also comprise a natural carrier. The carriers described herein are configured to form a three-dimensional framework to be injected or implanted into wound, defect, and/or surgical sites. In some embodiments, the wound may be an open wound or tunnel wound. The natural carriers are carriers that naturally occur in a placental membrane, and, for example, include extracellular matrices, such as collagen and hyuronic acid or elastin. In some embodiments, the decellularized placental membrane may exclude a non-naturally occurring carrier selected from the group consisting of gelatin, agarose, modified hyaluronic acid, propylene glycol alginate, polyethylene glycol, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linked or functionalized hyaluronan-based collagen and alginate, polyurethane, polylactic acid, or a combination comprising at least one of the foregoing polymers. In additional embodiments, the decellularized placental membrane and/or placenta-derived graft described herein may exclude salts of calcium, barium, aluminum, strontium, copper, zinc, magnesium, manganese, cobalt, or iron, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), acryl azide, and a combination thereof.

In some embodiments, the decellularized placental membrane and/or placenta-derived graft described herein does not comprise an additional crosslinker in addition to a natural carrier(s) from the placental membrane. In additional embodiments, the decellularized placental membrane and/or placenta-derived graft described herein does not comprise an additional carrier in addition to a natural carrier(s) from the placental membrane. For example, the decellularized placental membrane and/or placenta-derived graft described herein may not comprise alginate, propylene glycol alginate, native or crosslinked chitosan, starch, polyethylene glycol, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxylpectin, or carrageenan.

The decellularized placental membrane and/or placenta-derived graft may or may not include a carrier solution. The carrier solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The carrier solution may also comprise natural and or synthetic polymers selected from the group comprising native or modified collagen, gelatin, agarose, modified hyaluronic acid, fibrin, chitin, biotin, avidin, MATRIGEL®, proteoglycans, laminin, fibronectin, elastin, heparin, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, polylactic acid, or a combination comprising at least one of the foregoing polymers in addition to a natural carrier(s) from the placental membrane. In additional embodiments, for example, the decellularized placental membrane and/or placenta-derived graft described herein may or may not include a carrier in addition to a natural carrier(s) from the placental membrane, wherein the carrier is selected from the group consisting of native collagen, hyaluronic acid, fibrin, chitin, biotin, avidin, MATRIGEL®, proteoglycans, laminin, fibronectin, elastin, heparin, alginate, genipin, chitosan, starch, glucose or ribose, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxyl pectin, carrageenan, and a combination thereof. Moreover, in further embodiments, the decellularized placental membrane and/or placenta-derived graft described herein may or may not include a crosslinker in addition to a natural crosslinker(s) from the placental membrane, wherein the crosslinker is selected from the group consisting of alginate, starch, cellulose and its derivatives (such as cellulose acetate, carboxymethyl cellulose, and methyl cellulose), xanthan gum, dextran, carrageenan, genipin, hyaluronic acid, condroitin sulfate, locust bean gum, gum tragacanth, gum arabic, curdlan, pullulan, scleroglucan, and lower methoxylpectin. glucose or ribose, native collagen, hyaluronic acid, fibrin, chitin, biotin, avidin, MATRIGEL®, proteoglycans, laminin, fibronectin, elastin, heparin, chitosan, and a combination thereof.

In another aspect, the placenta-derived graft described herein consists essentially of and/or consists of the decellularized placental membrane. The term "essentially consisting of" defines the scope of the graft to include additional elements or agents that do not materially affect the protein composition and/or gelation of the placenta-derived graft without the elements or agents. For example, the placenta-derived graft consisting essentially of decellularized placental membrane may include elements in addition to the decellularized placental membrane that do not materially affect the protein composition and/or gelation of the placenta-derived graft consisting of the decellularized placental membrane. Materially affecting the protein composition herein means changing the protein composition at least by about 0.5, 1, 2, 3, 4, 5, 7, 9, 10, 12, 15, 20, 25, 30, or 40%. Materially affecting the gelation of the graft herein means changing the viscosity of the graft at least by about 0.5, 1, 2, 3, 4, 5, 7, 9, 10, 12, 15, 20, 25, 30, or 40%.

In another aspect, the methods described herein comprise treating the pre-decellularized placental membrane, decellularized placental membrane, and/or placenta-derived graft with one or more treatment solutions. In some embodiments, the method described herein may comprise treating the decellularized placental membrane and/or placenta-derived graft with one or more treatment solutions after freezing and/or freeze drying before implantation. In some embodiments, the treatment solution comprises an ionic, enzymatic, or chemical crosslinking agent, a photoactive agent, a polymer or a combination thereof. The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl suberimidate (DMS), and dimethyl-3-3'-dithiobispropionimidate (DTBP). The chemical crosslinking agent comprises one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid.

In another aspect, the method described herein may also comprise adding one or more bioactive supplement(s) to the pre-decellularized placental membrane, decellularized placental membrane, and/or placenta-derived graft. In some embodiments, the one or more bioactive supplement(s) is selected from a group consisting of a growth or differentiation factor of the FGF family, TGF-family, IGF-1, PDGF, EGF, VEGF, HGF, PTHrP, Ihh, dexamethasone, insulin, transferrin, selenium, ITS, or ascorbate. The bioactive supplements may be growth factors, differentiation factors, cytokines, anti-microbial agents, or anti-inflammatory agents. The growth or differentiation factors may be for example, a growth factor of the FGF-family or TGF-family, IGF-1, PDGF, EGF, VEGF, HGF, PTHrP, Ihh (Indian Hedgehog Homolog), dexamethasone, insulin, transferrin, selenium, ITS supplement, ascorbate, or a combination thereof. The cytokines may include GM-CSF, G-CSF, TNF-α, IL-1β, IL-4, IL-6, IL-8, IL-10, SLP1, MCP1, MIP-1α, MIP-2, IL-18, angiopoietin, KGF, endothelin, IFN-α, or IFN-β. Examples of anti-inflammatory agents may include an IL-1βR antibody, TNF-α receptor antagonist, cyclooxygenase-2 specific inhibitors, MAP kinase inhibitors, NO synthase inhibitors, NF-κB inhibitors, or inhibitors of MMP. There are various fibroblast growth factors. As an example, the human FGF-family includes 22 members, FGF-1 through FGF-23. (There is no human FGF-15 because FGF-15 is the mouse ortholog of human FGF-19.) Examples of members of the TGF-family may include TGF-α and TGF-β superfamily. The TGF-β superfamily includes TGF-βs (such as TGF-β1, TGF-β2, TGF-β3), activins, inhibins, bone morphogenic factors (BMPs), modified BMPs, anti-mullerian hormone (AMH), myostatins, and others. There are 20 isotypes of BMPs. They may be separated into four subfamilies, for example, (1) BMP2 and BMP4; (2) BMP3 and BMP3B (also known as growth/differentiation factor 10 (GDF10)); (3) BMPs 5, 6, 7 and 8; and (4) GDFs 5, 6, and 7. In additional embodiments, the method described herein may also comprise adding one or more bioactive supplement(s) extracted from tissue comprising demineralized bone matrix, basement membrane, or submucosa matrix. In further embodiments, the method described herein may also comprise adding one or more antioxidants including, for instance, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene to protect bioactive components from oxygen-radical-induced damage antioxidants.

In another aspect, the method described herein may also comprise adding one or more agent(s) that have bioactive supplement binding site(s) to the pre-decellularized placental membrane, decellularized placental membrane, and/or placenta-derived graft. In some embodiments, the agents having bioactive supplement binding site(s) may comprise hyaluronan, heparin, heparin sulfate, keratin sulfate, dermatan sulfate, chondroitin sulfate, betaglycan, heparan sulfate proteoglycan, syndecan, biglycan, or decorin. In additional embodiments, the agent(s) that have bioactive supplement binding site(s) increases the affinity of growth factors, differentiation factors, cytokines, anti-microbial agents, or anti-inflammatory agents to the pre-decellularized placental membrane, decellularized placental membrane, and/or placenta-derived graft.

In some embodiments, the weight percentage of the decellularized placental membrane in the placenta-derived graft is about 2, 5, 10, 15, 20, 30, 40, 50, 60, 70, 80, 90, 92, 94, 96, 98, 100% or more in a dry state based on the total weight of the placenta-derived graft. In additional embodiments, the weight percentage of the decellularized placental membrane in the placenta-derived graft is about 3, 5, 10, 15, 20, 30, 40, 50, 60, 70, 80, 90, 91, 93, 95, 97, 99, 100% or less in a dry state based on the total weight of the placenta-derived graft. In further embodiments, the weight percentage of the decellularized placental membrane in the placenta-derived graft is from about 2% to about 100%, from about 50% to about 90%, from about 50% to about 80%, from 60% to 100%, from 80% to about 100%, or from about 90% to about 100% in a dry state based on the total weight of the placenta-derived graft.

In another aspect, the invention relates to placenta-derived graft comprising a decellularized placental membrane comprising amnion and chorion layers that are separated or in contact. In another aspect, the invention also relates to placenta-derived grafts prepared by the methods described herein. In another aspect, the invention relates to scaffolds comprising the placenta-derived graft described herein. The scaffold may include an implant, which is a scaffold configured to be implanted in vivo.

In another aspect, the decellularized placental membrane is produced by removing less than about 1, 5, 10, 15, 20, 25. 30, 40, 50, 60, 70, or 80% of PDGF and/or bFGF from the pre-decellularized placental membrane at the area(s) in which amnion and chorion layers remain in contact. In some embodiments, concentration of PDGF and/or bFGF remains at least about 20, 30, 40, 50, 60, 70, 80, 90, 95, 98, or 99% of initial concentrations of PDGF and/or bFGF before the decellularization, respectively, at the area(s) in which amnion and chorion layers remain in contact. In some embodiments, the level of PDGF and/or bFGF in the decellularized placental membrane is at least about 10% to 300%, 10% to 200%, 10%-150%, or 10%-100% more than the sum of the levels of PDGF and/or bFGF in the decellularized control isolated amniotic membrane and decellularized control isolated chorionic membrane having the substantially identical area size after decellularization. In additional embodiments, the placenta-derived graft described herein may comprise type I collagen, type IV collagen, laminin gamma-1, fibronectin, chorionic somatomammotropin, FGF-12, FGF-13, IGF-2, EGFL-7, PDGF-AA, EGF, PlGF, GCSF, and bFGF. In some embodiments, the concentration of the type I collagen in the placenta-derived graft is about 20, 25, 30, 31, 32, 33, 34, 35, 36, 37, 38, 39, 40, 45% or more; about 20, 25, 30, 31, 32, 33, 34, 35, 36, 37, 38, 39, 40, 45% or less; and/or about between 20 and 50%, between 25 and 45%, between 30 and 40%, or between 33 and 38%, based on total weight of the graft.

The placenta-derived graft described herein may be rich in ECM proteins and glycoproteins found throughout the body, which play a vital role in driving key cellular events such as cell migration, adhesion, differentiation, proliferation, and survival. Proteins present in the placenta-derived graft, such as collagen IV, the most common type of collagen found in the human basement membrane, laminins, fibronectin, and proteoglycans (e.g. heparan sulfate), may provide the basement membrane with a tensile strength capable of supporting cells, binding cells to the underlying collagenous matrix and separating epithelia from mesenchyme/underlying connective tissue. In some embodiments, the decellularized placental membrane has at least 10, 20, 30, 40, 50, 60, 70, 80, 90, 100% or more porosity than the pre-decellularized placental membrane. In one aspect, the lyophilized, dehydrated or freeze-dried placenta-derived graft or decellularized placental membrane has a density in the range of 0.001 to 0.1 mg/mm$^2$, 0.005 to 0.1 mg/mm$^2$, or 0.01 to 0.1 mg/mm$^2$. In another embodiment, the lyophilized, dehydrated or freeze-dried placenta-derived graft has the density in the range of 0.005 to 0.2 mg/mm$^3$, 0.01 to 0.2 mg/mm$^3$, 0.05 to 0.2 mg/mm$^3$, or 0.05 to 0.15 mg/mm$^3$.

In another aspect, the invention relates to methods of cell culture comprising culturing cells in the presence of the placenta-derived graft or the decellularized placental membrane of the present invention. The placenta-derived graft or the decellularized placental membrane may provide two-dimensional or three-dimensional scaffolds. The cultured cells may be in the placenta-derived graft or the decellularized placental membrane. As used herein, cell culture refers to the maintenance of cells in an artificial environment, commonly referred to as an in vitro environment. The term cell culture is a generic term and may be used to encompass the cultivation not only of individual cells, but also of tissues, organs, organ systems or whole organisms. The cells used in the culture methods disclosed herein can be any prokaryotic or eukaryotic cell. The cell type used in the culture methods disclosed herein need not be from the same species from which the cell support compositions derive. In addition, the cells may be from an established cell line, or they may be primary cells or genetically engineered cells. For example, the cells may be selected from the group consisting of stem cells, adipose derived stem cells, dorsal root ganglion cells, pancreatic beta islet cells, cardiomyocytes, hepatocytes, iPSCs, cancer cells, and umbilical vein endothelial cells.

For example, the invention provides for growing and/or culturing cells on or in the placenta-derived graft or decellularized placental membrane described herein. "Growing and/or culturing cells on or in the placenta-derived graft described herein" includes traditional cell culture methods as well as placing on a surface of the placenta-derived graft described herein in any setting, such as in natural or synthetic biocompatible matrices or tissues. The cells may be mammalian, such as but not limited to human, bovine, porcine, murine, ovine, equine, canine, feline and others. In some embodiments, the cells that are cultured on or in the placenta-derived graft or decellularized placental membrane described herein are stem cells. As used herein, a stem cell is used as it is in the art and means a cell that has the ability to divide and give rise to one daughter cell that may be at least partially differentiated and to another daughter cell that retains the developmental potential of the mother cell. As used herein, stem cells can be adipose derived stem cells, dental pulp stem cells, adult stem cells (ASCs), embryonic stem cells (ESCs), tissue-specific progenitor cells, and/or induced pluripotent stem cells (iPSCs). The ASCs may include, but is not limited to, hematopoietic stem cells, mammary stem cells, intestinal stem cells, mesenchymal stem cells, endothelial stem cells, neural stem cells, olfactory adult stem cells, neural crest stem cells, and testicular cells. In further embodiments, the placenta-derived graft described herein may be used in in vitro methods for supporting cell growth and proliferation as well as for increasing maintenance or facilitating differentiation, such as osteogenesis, chondrogenesis, or ligament/tendon genesis, in the stem cells cultured on or in the placenta-derived graft described herein.

In some embodiments, the cells that are cultured on or in the placenta-derived graft or decellularized placental membrane described herein may be cardiomyocytes, human umbilical vein endothelial cells (HUVEC), induced pluripotent stem cell (iPSC), hepatocytes, osteoblasts, chondrocytes, dorsal root ganglia (DRG) cells, mesenchymal stem cells, adipose-derived stem cells, embryonic stem cells, progenitor cells, differentiated cells, undifferentiated cells, and/or -pluripotent stem cells. Appropriate cells may also include, but are not limited to cells of the ectodermal lineage, cells of the mesodermal lineage, and cells of the endodermal lineage. Examples of cells of the ectodermal lineage include but are not limited to keratinocytes, neurons. Examples of cells of the mesodermal lineage include but are not limited to myoblasts, adipocytes, fibroblasts, endothelial cells, osteoblasts, chondrocytes, or stromal cells. Examples of cells of the endodermal lineage include but not limited to epithelial cells of the auditory tube, the respiratory tract, such as trachea, bronchi, and alveoli of the lungs, the gastrointestinal tract, the urinary bladder and epithelial cells lining all glands. The cells may also be primary cells derived from tissues or organs. Appropriate cell lines used in the present invention may include but are not limited to mesenchymal cell lines, preosteoblastic cell lines, osteoblastic cell lines, and chondroblastic cell lines.

In some embodiments, the cells may be derived from autologous or allogeneic sources. The cells may be differentiated cells including chondrocytes, osteoblasts, osteoclasts, endothelial cells, epithelial cells, fibroblasts, and periosteal cells. Additionally, the cells may be totipotent, pluripotent, multipotent, progenitor cells, tissue-specific progenitor cells, or adult somatic stem cells. The stem cells may be derived from embryos, placenta, bone marrow, adipose tissue, blood vessel, amniotic fluid, synovial fluid, synovial membrane, pericardium, periosteum, dura, peripheral blood, umbilical blood, placental membrane, menstrual blood, teeth, nucleus pulposus, brain, neonatal foreskin, skin, hair follicle, intestinal crypt, neural tissue, liver, pancreas, or muscle. The cells may be derived from skeletal muscle, smooth muscle, and cardiac muscle. The stem cells may be derived from genetic reprogramming of mature cells, such as induced pluripotent stem cells (iPSCs). All cells may further be derived from living or recently deceased donors.

Any cell described herewith may be cultured on or in the placenta-derived graft or decellularized placental membrane described herein for between about 15 minutes and about one year, about 15 minutes and about 6 months, about 15 minutes and about 3 months, about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30°

C. and about 37° C., in an atmosphere containing between about 1% $CO_2$ and about 10% $CO_2$ or about 4% $CO_2$ and about 6% $CO_2$, in certain embodiments. In some embodiments of the present invention, cells may be cultured in the absence or presence of one or more growth factors described herein and (1) a tissue or an organ, (2) a matrix, or (3) a combination thereof. Cells that have been cultured in the absence or presence of one or more growth factors described herein in a cell culture medium may subsequently be applied to a matrix, a tissue, an organ or a combination thereof, in certain embodiments.

The method of cell culture may further comprise storing the cells on or in the placenta-derived graft or decellularized placental membrane. In some embodiments, the cells on or in the placenta-derived graft are stored at room temperature (i.e. about 24° C.), at about 4° C., at about −20° C. or in cryopreservation. In other embodiments, the cells on or in the placenta-derived graft are stored at a temperature from about −200, −180, −100, −50, −45, −40, −35, −30, −25, −20, −10, −5, 0, 1, 2, 3, 4, 5, 10, 20, 21, 22, 23, 24, 25, 26, 27, 28, 29, 30, 35, 36, 37, 38, or 39° C. to about −150, −140, −130, −90, −40, −35, −30, −25, −20, −15, −10, 0, 1, 2, 3, 4, 5, 6, 7, 8, 9, 10, 15, 25, 30, 35, 36, 37, 38, or 40° C. In other embodiments, the cells on or in the placenta-derived graft or decellularized placental membrane are stored at a temperature from about −200 to 50° C., from about −160 to 36° C., from about −160 to 25° C., from about −160 to 5° C., from about −5 to 23° C., from about 0 to 30° C., or from about 15 to 40° C.

In another aspect, the invention relates to methods of promoting differentiation of the stem cells (e.g., pluripotent stem cells) or tissue-specific progenitor cells described herein, the method comprising culturing the stem cells or tissue-specific progenitor cells in the presence of an effective amount of the placenta-derived graft or decellularized placental membrane prepared by the method described herein. The stem cells (e.g., pluripotent stem cells) or tissue-specific progenitor cells may be on or in the placenta-derived graft or decellularized placental membrane. For example, the stem cells (e.g., pluripotent stem cells) or tissue-specific progenitor cells may be differentiated into osteoblasts, chondrocytes, cardiomyocyte, pancreatic cells, neuronal cells, ligament or tendon. In some embodiments, the tissue-specific progenitor cells are differentiated into a tissue of interest without adding a growth factor. In another aspect, the invention also relates to methods of promoting vascular, myogenic, or neurogenic differentiation of the stem cells or tissue-specific progenitor cells, the method comprising culturing the stem cells or tissue-specific progenitor cells on or in the placenta-derived graft or decellularized placental membrane described herein.

In some embodiments, the placenta-derived graft described herein may be used in in vitro methods for extending the maintenance of stemness in tissue-specific progenitor cells (i.e. ability to proliferate and/or differentiate into a specific tissue through extended culture) and/or self-renewing ability of the tissue-specific progenitor cells, the method comprising culturing the tissue-specific progenitor cells on or in the placenta-derived graft, optionally without adding a growth factor or another secondary factor to induce the maintenance of the cells. In further embodiments, the placenta-derived graft described herein may also be used in in vitro or in vivo methods for promoting differentiation of pluripotent stem cells without adding additional growth factors or another secondary factor to induce the differentiation of the cells. In other embodiments, the placenta-derived graft described herein may also be used in in vitro or in vivo methods for promoting differentiation of pluripotent stem cells and/or tissue-specific progenitor cells with an addition of one or more growth factors or other secondary factors to induce the maintenance or differentiation of the cells. In additional embodiments, the placenta-derived graft described herein may also be used in in vitro or in vivo methods for enhancing the effect of one or more growth factors or other secondary factors to induce the maintenance or differentiation of the cells in promoting differentiation of pluripotent stem cells and/or tissue-specific progenitor cells.

For example, the invention also relates to methods of promoting osteoinductivity, with the methods comprising culturing cells on or in the placenta-derived graft described herein. As used herein, "osteoinductivity" can refer to causing cells to differentiate into cells that are more osteoblast-like or periosteal cell-like in phenotype, or the term can refer to increasing the proliferation of osteoblasts, periosteal cells, or both. The cells, prior to culture on or in the placenta-derived graft, may be undifferentiated or partially differentiated cells. The cells may be present in culture or in a tissue, organ or portion thereof or in an organism. The osteoinductive activity of the placenta-derived graft may or may not be altered, including but not limited to, enhanced activity, relative to a control surface.

In one aspect, the invention also relates to methods of repairing a defect in or on a tissue comprising covering or contacting the site of defect with an effective amount of the placenta-derived graft or decellularized placental membrane described herein. The repair methods may comprise implanting the placenta-derived graft described herein on the site of defect. The tissues with the defect may be bone tissues, cartilage, soft tissue, spinal cord, dura mater, membrane, and mucosa. Examples of soft tissues with the defect may include tendon, ligament, dermis, skin, vocal cord, nerve, bladder, vagina, urethral, heart, subcutaneous tissue, fascia, breast, muscle, placental membrane, placenta, and rotator cuff. In another aspect, the tissues with the defect may be in the musculoskeletal system, digestion system, cardiovascular system, respiratory system, urinary system, reproductive system, nervous system, and/or immune system. In some embodiments, the method excludes rehydration of the placenta-derived graft prior to implanting to allow said placenta-derived graft to absorb blood, fluid, and/or autologous cells in situ. Alternatively, implantation of a placenta-derived graft into a human or animal can be conducted by re-hydrating the placenta-derived graft with a rehydrating solution; optionally seeding vital cells on the placenta-derived graft to render the placenta-derived graft vital; optionally culturing the cell-seeded placenta-derived graft before implantation; and implanting the placenta-derived graft on the defect. In some embodiments, the rehydrating solution comprises one or more selected from the group consisting of blood or bone marrow aspirate, platelet rich plasma, cerebrospinal fluid, synovial fluid, enzymes, bioactive supplements, natural polymers, synthetic polymers, photoactive agents, antioxidants, crosslinking agents, antimicrobial agents, vital cells, and one or more agents that have bioactive supplement binding site(s). In additional embodiments, the vital cells comprise one or more selected from the group consisting of cells from autologous or allograft bone marrow aspirate; stromal cells from bone marrow; stromal cells from fat, synovium, periostieum, perichondrium, muscle, dermis, umbilical cord blood, placenta, placental membrane, and Warton's jelly; and pericytes. The invention also relates to methods of promoting angiogenesis, hemostatic, biocompatibility, infection resistance, anti-inflammatory, anti-scarring, attachment, proliferation or maintaining the differentiated state or preventing de-differentiation of osteoblasts, chondrocytes, ligament cells, tendon cells, fibroblasts, adipocytes, and/or any cell type disclosed herein with the methods comprising placing the placenta-derived graft described herein at the defect site.

The invention also relates to methods of promoting chondroinductivity, with the methods comprising culturing cells in the presence of an effective amount of a placenta-derived graft or decellularized placental membrane described herein. As used herein, "chondroinductivity" can refer to causing cells to differentiate into cells that are more chondrocyte-like in phenotype, or the term can refer to increasing the proliferation of chondrocytes, or both. The cells, prior to culture on or in the placenta-derived graft, may be undifferentiated or partially differentiated cells. The cells may be present in culture or in a tissue, organ or portion thereof or in an organism. The chondroinductive activity of the placenta-derived graft or decellularized placental membrane may or may not be altered, including but not limited to, enhanced activity, relative to a control surface.

The invention also relates to methods of promoting ligament/tendon differentiation, with the methods comprising culturing cells in the presence of an effective amount of a placenta-derived graft or decellularized placental membrane described herein. As used herein, "ligament/tendon differentiation" can refer to causing cells to differentiate into cells that are more ligament and/or tendon-like in phenotype, or the term can refer to increasing the proliferation of ligament and/or tendon, or both. The cells, prior to culture on or in the placenta-derived graft, may be undifferentiated or partially differentiated cells. The cells may be present in culture or in a tissue, organ or portion thereof or in an organism. The ligament/tendon differentiation activity of the placenta-derived graft or decellularized placental membrane may or may not be altered, including but not limited to, enhanced activity, relative to a control surface.

There are varieties of osteoblast, chondrocyte, ligament/tendon differentiation markers that can be measured to assess osteoinductivity, chondroinductivity, or ligament/tendon differentiation, respectively. For example, cells express alkaline phosphatases during the early stages of differentiation toward osteoblast lineages. Therefore, in vitro alkaline phosphatase assays may be used to evaluate osteoinductivity in cells cultured in the presence of an effective amount of a placenta-derived graft or decellularized placental membrane described herein. The ability of the placenta-derived graft to stimulate or induce the alkaline phosphatase expression in an otherwise non-bone forming cells, such as myoblast (C2C12 cells), would indicate that the placenta-derived graft has osteoinductive activity. In these assays, cells cultured on or in the placenta-derived graft and on a control surface are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" surface of the placenta-derived graft would simply cause an increase in the osteoblastic markers in experimental cells. Similarly, chondrocyte markers, including but not limited to type X collagen, type II collagen, Sox 9, Aggrecan. Matrilin-1 and CEP-68, to name a few, can be used to assess chondroinductive potential. Moreover, ligament/tendon markers, including but not limited to scleraxis, can be used to assess ligament/tendon differentiation potential.

Moreover, osteoinductivity, chondroinductivity, and ligament/tendon differentiation may be determined in tissue culture by investigating the ability of the placenta-derived graft or decellularized placental membrane to differentiate or induce osteoblast phenotype, chondrocyte phenotype, ligament/tendon cell phenotype in cultured cells, such as primary cells, cell lines, or explants. For example, the cells may display increased production of a marker characteristic of osteoblasts, such as alkaline phosphatase, etc. For example, the osteoinductive, chondroinductive, ligament/tendon differentiation potentials of the placenta-derived graft or decellularized placental membrane may be more than 0.2, 0.4, 0.6, 0.8, 1, 2, 3, 4, 5, 6, 7, 8, 9 or 10 times greater than a control. In another example, the osteoinductive, chondroinductive, ligament/tendon differentiation potentials of the placenta-derived graft or decellularized placental membrane described herein may be more than 10, 20, 30, 40, 50, 60, 70, 80, 90, 100, 500 or even 1000 times greater than those of a control scaffold.

Osteoinductivity, chondroinductivity, ligament/tendon differentiation, for assessing the bone, cartilage, ligament or tendon forming potential induced by the placenta-derived graft or decellularized placental membrane in a location such as muscle, may also be evaluated using a suitable animal model. For example, intramuscular implantation into a rodent has been used as a model to assess osteoinductive activity of the placenta-derived graft or decellularized placental membrane.

The invention also relates to methods of promoting cell angiogenesis, hemostatic, biocompativlity, infection resistance, anti-inflammatory, anti-scarring, attachment, proliferation or maintaining the differentiated state or preventing de-differentiation of osteoblasts, chondrocytes, ligament cells, tendon cells, fibroblasts, adipocytes, and/or any cell type disclosed herein with the methods comprising culturing the cells in the presence of a placenta-derived graft or decellularized placental membrane described herein. The proliferative activity of the placenta-derived graft or decellularized placental membrane may or may not be altered, including but not limited to, enhanced activity, relative to a control surface. The invention further relates to methods of promoting adipose tissue formation of adipocytes, fibroblasts, epithelial cells, and/or vascular endothelial cells. The invention also relates to methods of increasing or promoting angiogenesis, hemostatic function, biocompatibility, anti-scarring, anti-inflammatory, and/or infection resistance, Mitogenicity may be assessed by investigating cell proliferation induced by the placenta-derived graft or decellularized placental membrane using various in vitro assays that measure metabolic activity, such as MTT [3-(4,5-dimethyl-thiazol-2-yl)-2,5-diphenyltetrazolium bromide assay, alamarBlue® assay, and others. The alamarBlue® assay uses a non-cytotoxic reduction-oxidation indicator to measure cell metabolic activity, making it a nondestructive assay for assessing the mitogenic activity of the placenta-derived graft described herein. Proliferation can also be assessed by measuring DNA quantification, such as by using a PicoGreen™ DNA assay, radioactive labeling of DNA synthesis, such as [$^{3H}$]thymidine labeling or BrdU incorporation. Proliferation can also be assessed via manual cell counting, such as staining cells with trypan blue and counting with a hemacytometer.

The invention also relates to methods of increasing or promoting osteogenesis, chondrogenesis, or ligament/tendon genesis in cells. The methods may comprise culturing the cells on or in the placenta-derived graft or decellularized placental membrane described herein. As used herein, "osteogenesis" is the deposition of new bone material or formation of new bone, including, but not limited to, intramembranous osteogenesis and endochondral osteogenesis. As used herein, "chondrogenesis" is the deposition new cartilage material or formation of new cartilage. As used herein, "ligament/tendon genesis" is the deposition new ligament and/or tendon material or formation of new ligament and/or tendon. The osteogenic, chondrogenic, ligament, or tendon inducing activity of the placenta-derived graft or decellularized placental membrane may or may not be altered, including but not limited to, enhanced activity, relative to a control surface. The cells may include cells in any tissue in which bone, cartilage, ligament, or tendon formation is desired, such as, but not limited to, bone, cartilage, ligament, muscle, tendon, etc.

Example 1. Preparation of Pre-Decellularized Placental Membrane after Recovery

Human term placenta and amniotic sac with donor's consent were obtained after caesarean section and transferred to the processing facility under sterile condition.

The amniotic sac comprising placental membrane with both amniotic and chorionic membrane layers were cut around the placenta skirt and rinsed at least three times with isotonic solution such as saline, or Lactated Ringer to remove loosely bond blood. The rinsed placental membrane with both amnion and chorion layers in contact was laid on a sterile board with amniotic membrane epithelia layer facing up. Different sizes and shapes of mesh frames were laid on top of the placental membrane. The placental membrane was cut to different sizes and shapes aligned with the sizes and shapes of the matching frames. Each piece of the placental membrane with both amniotic and chorionic membrane layers were fixed with the mesh frames using sutures or clips (FIG. 1). The prepared placental membrane pieces were placed flat in sterile containers and stored at −20° C. or −80° C. freezer until further processing. Accordingly, the pre-decellularized placental membrane was prepared.

Example 2. Cell Removal from Pre-Decellularized Placental Membrane—Decellularization Method 1: Different placental membrane pieces along with the frames were thawed at ambient temperature, weighed aseptically, and placed in separate sterile flasks. The placental membrane pieces were rinsed with isotonic saline at five minutes each for three times with agitation, followed by blotting tissue with sterile absorbant towels and placed back to sterile flasks. Prepared devitalization solution containing sodium lauroyl sarcosinate and DNAase in Tris buffer was added to the flasks according to the weight of tissue and the flasks were agitated for 2 hours at ambient temperature. The devitalization solution was removed and placental membrane was blot with sterile absorbant towels to remove excess fluid. Placental membrane pieces were placed back into the flasks and rinsed with isotonic saline for one hour, followed by two more saline rinses at 1 hour each with agitation. After saline rinse, placental membrane pieces were rinsed with sterile ultrapure water at fifteen minutes each for three times with agitation (Item A in FIG. 2).

Method 2: Different placental membrane pieces along with frames were thawed at ambient temperature, weighed aseptically, and placed in separate sterile flasks. The placental membrane pieces were rinsed with red blood cell lysis buffer containing Tris-HCl and $NH_4Cl$ for 15 minutes at ambient temperature with agitation, followed by rinsing with isotonic saline at five minutes each for three times with agitation. Prepared devitalization solution containing sodium lauroyl sarcosinate and DNAase in Tris buffer was added to the flasks and the flasks were agitated for 2 hours at ambient temperature. The devitalization solution was removed and placental membrane was blot with sterile absorbant towels to remove excess fluid. Placental membrane pieces were placed back into the flasks and rinsed with isotonic saline for one hour, followed by another saline rinse for overnight with agitation. After saline rinse, placental membrane pieces were rinsed with sterile ultrapure water for fifteen minutes each for three times with agitation.

Figure 2:
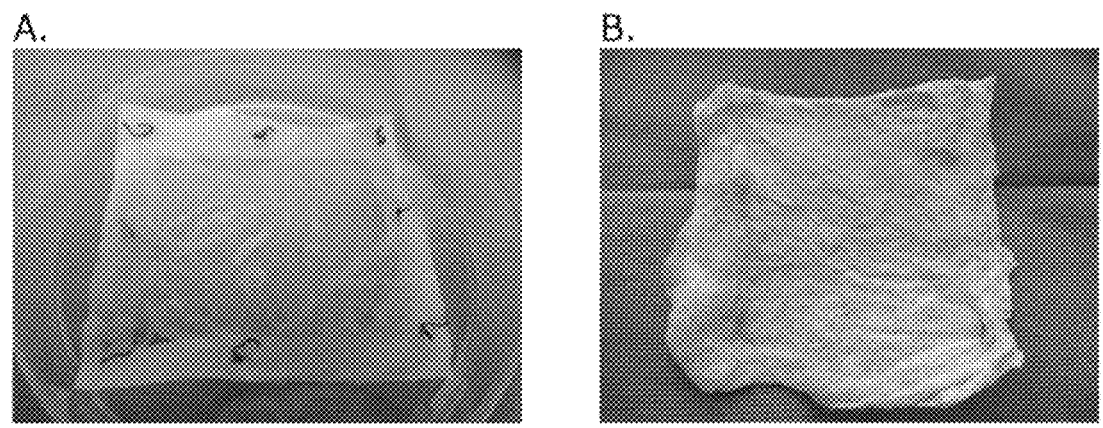
FIG. 2 depicts exemplary decellularized placental membranes sutured on fixture after cleaning and cell removal (A) and freeze drying (B).

The decellularized placental membrane prepared with either method 1 or method 2 were placed in sterile container and freeze-dried for 48-96 hours (Item B in FIG. 2).

Example 3. Characterization of Decellularized Placental Membrane

Decellularized placental membrane pieces were prepared according to the processing steps described in Example 1, and Example 2. Representative samples were punched out of pre-decellularized or decellularized placental membrane for the following characterization.

Figure 3:
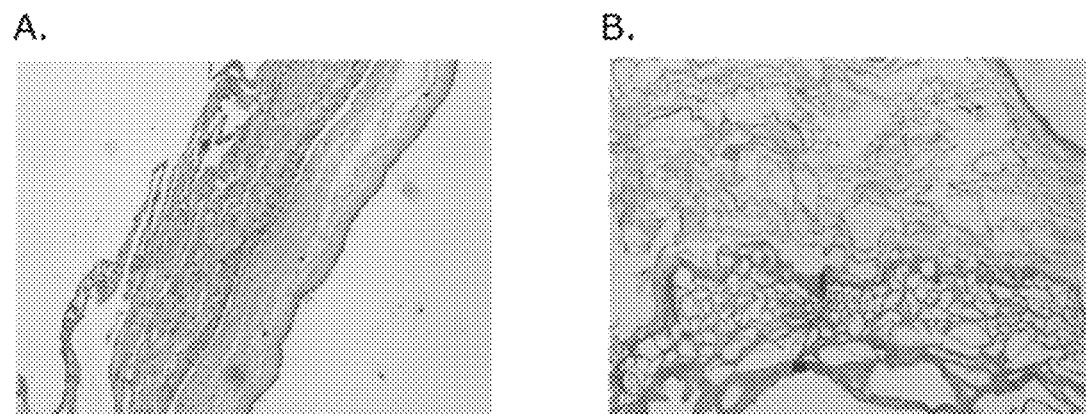
FIG. 3 depicts exemplary placental membranes pre-decellularization (A) and decellularization (B) stained with H&E (10×).

Histology of decellularized placental membrane: Representative samples from pre-decellularized placental membrane with or without cleaning and decellularization were fixed in 10% neutral buffered formalin followed by dehydration/cleaning/paraffin infiltration. Each sample was bisected and embedded with the both cross section faces facing down. The tissue was sectioned at 5 micron for staining. The Hematoxylin and eosin staining showed cell removal in post cleaning/decellularization process (FIG. 3). In conclusion the decellularization process efficiently removed the cells from intact pre-decellularized placental membrane with both methods Residual DNA in decellularized placental membrane: Representative samples from placental membrane with or without cleaning and decellularization were used for proteinase K digestion and DNA quantification using a PicoGreeen® DNA assay kit (Invitrogen P11496) following LifeNet Health standard operation protocol. PicoGreen dsDNA reagent is an ultra sensitive fluorescent nucleic acid stain for quantifying double-stranded DNA (dsDNA) in solution. The measured and calculated results were expressed as percent dsDNA reduction compared to the pre-decellularized placental membrane from the same donor. The average percent DNA removal from 6 individual donors was 94.7±2.34%.

Figure 4:
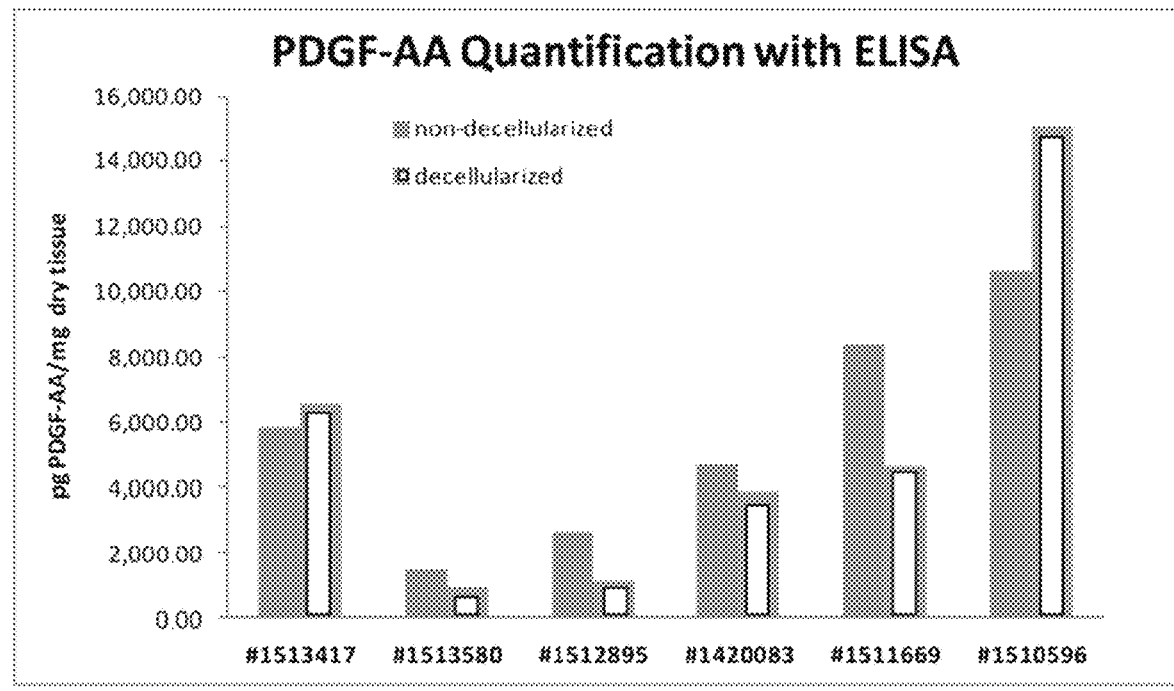
FIG. 4 depicts PDGF-AA quantification in exemplary pre-decellularized and decellularized placental membranes.
Figure 5:
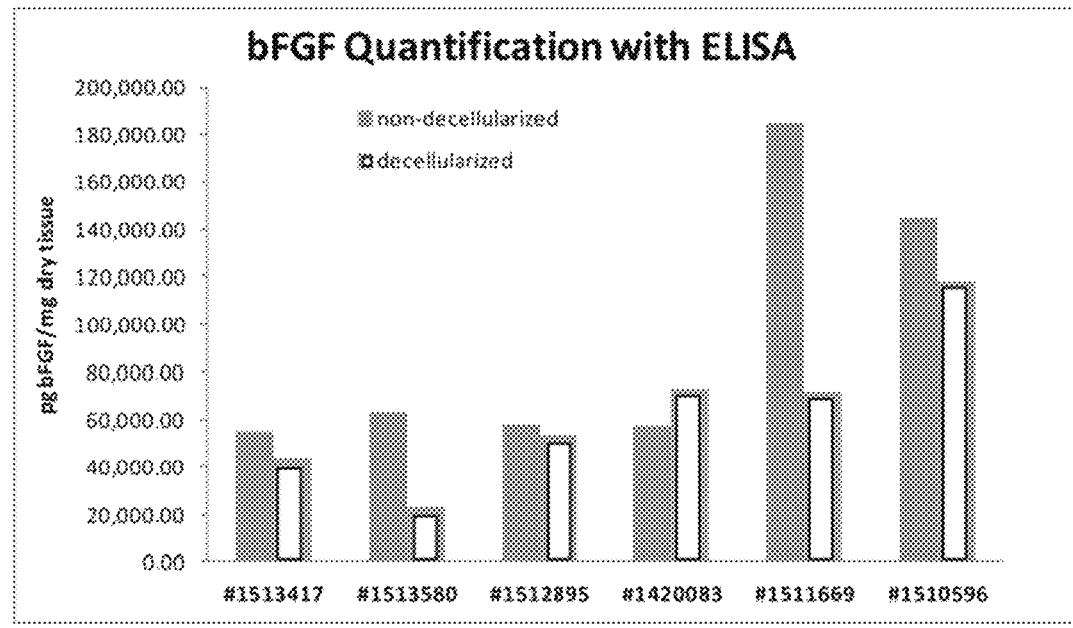
FIG. 5 depicts bFGF quantification in exemplary pre-decellularized and decellularized placental membranes.

Growth factors in decellularized placental membrane: Representative samples from placental membrane with or without cleaning and decellularization were cut to small pieces and incubated with HEPES buffer containing collagenase, hyaluronidase, protease inhibitors, and Triton X-100 for 20-24 hours at 37° C. with agitation. The resulting samples were sonicated briefly and followed by centrifugation at 10,000 g for 15 minutes at 4° C. The supernatant were aliquoted and used for growth factor quantification following instructions of ELISA kits for bFGF and PDGF-AA (Ray Biotech, Inc.). The bFGF and PDGF-AA results from 6 individual donors were calculated and showed in FIGS. 4 and 5.

Example 4. Subcutaneous Implantation of Decellularized Placental Membrane

The decellularized placental membrane is prepared as described in Example 1-2. Implant samples are generated by taking 8 mm biopsy punches from the freeze dried or non-freeze-dried placental membrane. Half of samples are terminally sterilized by gamma irradiation at 10-20 kGy absorbed dose on dry ice.

Male athymic mice (Nu/Nu Foxn1nu), about 6 weeks in age, are used for this study. The animals are weighed to the nearest 0.1 g and anesthesia is induced by isoflurane (1 to 5% in O2 to effect) and maintained at 2 to 3% in $O_2$ for the surgery. Each animal receives peri-operative analgesic Buprenorphine SR® at 0.5 to 1.0 mg/kg via subcutaneous injection and ophthalmic ointment is placed over the eyes. The dorsal region is swabbed twice with betadine and alcohol. An approximately 1 cm incision, one on each side of the dorsal midline is created. Two subcutaneous pockets approximately 0.15 cc are formed from these incisions using blunt dissection. The implant samples of decellularized placental membrane are rehydrated with isotonic saline for a minimum of 5 minutes prior to implantation. The implants are inserted in the subcutaneous pocket and a suture is placed between one edge of implanted placental membrane and adjacent mouse muscle to help locate the implanted sample. Each animal receives a total of 2 implants. Incisions are closed with interrupted 4-0 prolene sutures. Each animal is housed separately in a clean cage and monitored until the animal is alert and mobile.

After 2 or 4 weeks of implantation, animals are euthanized by $CO_2$ inhalation and their weights are recorded. The implant sites were carefully exposed by cutting the skin and subcutaneous tissues about 5 mm away from the implant. The implanted sample and the 3-5 mm of surrounding tissue were excised and fixed in 10% neutral buffered formalin (NBF) for a minimum of 4 days to achieve complete fixation.

Each explant sample is cut along its longest midline to create two halves. The resulting specimens are embedded together (cut face down) in the same paraffin block and histology sections are prepared. Two sections from each group are stained with hematoxylin and eosin (H&E). The section with the largest cross section area of implant material is used for grading. Tissue sections are evaluated semi-quantitatively for fibroblast infiltration of the implant, degree of neovascularization, inflammatory cell response (macrophage/giant cells, neutrophils), and fibrous tissue/encapsulation. Fibroblast infiltration and angiogenesis can be found in the implanted placental membrane. None or minimum inflammation will be found in the implanted placental membrane Example 5. Rabbit Urethroplasty with Decellularized Placental Membrane The decellularized placental membrane is prepared as described in Example 1-2. Implant samples are generated by cutting 1 cm×2 cm pieces from the freeze dried or non-freeze-dried placental membrane. Half of samples are terminally sterilized by gamma irradiation at 10-20 kGy absorbed dose on dry ice.

Male New Zealand white rabbits (3-3.5 kg, 3-4 month of age) are used for this study. Rabbits are weighed to the nearest 10 g and anesthetized with ketamine (35 mg/kg, IM) and xylazine (5 mg/kg, IM) and will be on isoflurane (2 to 3% in $O_2$) for the duration of the surgical procedure. Following urethral catheterization, the penile urethra is exposed through a ventral midline skin incision and mobilized from the underlying corpora spongiosum. A 1×2 cm$^2$ (Width×Length) area of ventral urethral tissue is excised and a placental membrane of equal size is anastomosed to the defect site using interrupted 6-0 polyglactin sutures. Non absorbable 6-0 polypropylene sutures are placed at the proximal, distal, and lateral boundaries of the implantation area for identification of graft borders. Skin incisions are subsequently closed with running sutures. In addition, a control group of animals (N=3) receiving urethrotomy alone was treated similarly in parallel. The animals will be given 1 dose of buprenex SR (0.12 mg/kg, SQ) after the procedure and an antibiotic, Baytril (5 mg/kg, IM) for 7 days after the procedure. For all experimental groups, an 8 French Firlit-Kluge urethral stent (Cook Urological, Spencer, Ind.) is secured to the urethra to allow for reinforcement of the repair site and free urine drainage via catheterization for 7 days following surgical procedures. After stent removal, animals are allowed to void voluntarily until the completion of the study. After three months the rabbits undergo a cystourethroscopy under general anesthesia to evaluate urethral patency. Controls and rabbits receiving implants are euthanized at 3 months post-implantation and isolated urethral specimens are subjected to histological, immunohistochemical, and histomorphometric analyses. Re-epithelialization on placental membrane towards to the lumen will be expected after 3 months of implantation.

Example 6. Cell Removal from Isolated Amniotic Membrane, Chorionic Membrane, and Intact Placental Membrane—Decellularization Human term placenta and amniotic sac with donor's consent were obtained after caesarean section and transferred to the processing facility under sterile condition.

Figure 9:
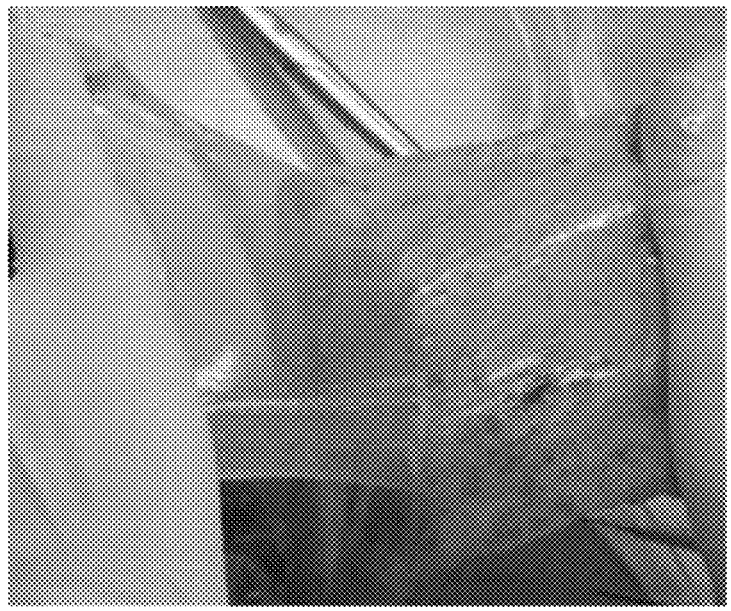
FIG. 9 depicts isolate pre-decellularized amniotic membrane (AM) isolated from pre-decellularized chorionic membrane (CM).

The amniotic sac comprising placental membrane with both amniotic and chorionic membrane layers were cut around the placenta skirt and rinsed at least three times with isotonic solution such as saline, or Lactated Ringer to remove loosely bond blood. The rinsed placental membrane was laid on a sterile board and cut to half. The amniotic membrane was isolated from the attaching chorionic membrane for one half of the placental membrane (FIG. 9). The amniotic membrane was laid on the board with epithelial cells facing down and the chorionic membrane was laid on the board with the trophoblast layer facing down. Different sizes and shapes of mesh frames were laid on top of the isolated amniotic membrane or isolated chorionic membrane. The membrane was cut to different sizes and shapes aligned with the sizes and shapes of the matching frames. Each piece of the isolated amniotic membrane or chorionic membrane were fixed with the mesh frames using clips. Another half of the placental membrane was remained intact and laid on board with amniotic membrane epithelia layer facing up. Different sizes and shapes of mesh frames were laid on top of the intact placental membrane. The placental membrane was cut to different sizes and shapes aligned with the sizes and shapes of the matching frames. Each piece of the intact placental membrane with both amniotic and chorionic membrane layers were fixed with the mesh frames using clips. The prepared intact or isolated placental membrane pieces were placed flat in sterile containers and stored at −80° C. freezer until further processing. Different intact or isolated placental membrane pieces along with frames were thawed at ambient temperature, weighed aseptically, and placed in separate sterile flasks. The placental membrane pieces were rinsed with red blood cell lysis buffer containing Tris-HCl and $NH_4Cl$ for 15 minutes at ambient temperature with agitation, followed by rinsing with isotonic saline at five minutes each for three times with agitation. Prepared devitalization solution containing sodium lauroyl sarcosinate and DNAase in Tris buffer was added to the flasks and the flasks were agitated for 2 hours at ambient temperature. The devitalization solution was removed and the intact and isolated placental membrane was blot with sterile absorbent towels to remove excess fluid. Placental membrane pieces were placed back into the flasks and rinsed with isotonic saline for half hour for three times with agitation. After saline rinse, placental membrane pieces were rinsed with sterile ultrapure water for fifteen minutes each for three times with agitation.

The decellularized isolated amniotic membrane, isolated chorionic membrane, and intact placental membrane from five different donors prepared as shown above were placed in sterile container and freeze-dried for 48-96 hours.

Example 7. Characterization of Decellularized and Isolated Amniotic Membrane, Chorionic Membrane, and Intact Placental Membrane Decellularized placental membrane pieces were prepared according to the processing steps described in Example 6. Representative samples were punched out of amniotic membrane, chorionic membrane, and intact placental membrane prior to and after cleaning/decellularization steps for the following characterization.

Residual DNA in decellularized amniotic membrane, chorionic membrane, and intact placental membrane: Representative samples from amniotic membrane, chorionic membrane and intact placental membrane with or without cleaning and decellularization were used for proteinase K digestion and DNA quantification using a PicoGreeen® DNA assay kit (Invitrogen P11496) following LifeNet Health standard operation protocol. PicoGreen dsDNA reagent is an ultra sensitive fluorescent nucleic acid stain for quantifying double-stranded DNA (dsDNA) in solution. The measured and calculated results were expressed as percent dsDNA reduction compared to the non-decellularized amniotic membrane, chorionic membrane, and intact placental membrane from the same donor. The average percent DNA removal from 5 individual donors was 95.96±2.03%, 95.79±5.56%, and 93.74±5.07% for isolated amniotic membrane, isolated chorionic membrane, and intact placental membrane, respectively. There was no significant difference among these groups (p>0.05).

Figure 10:
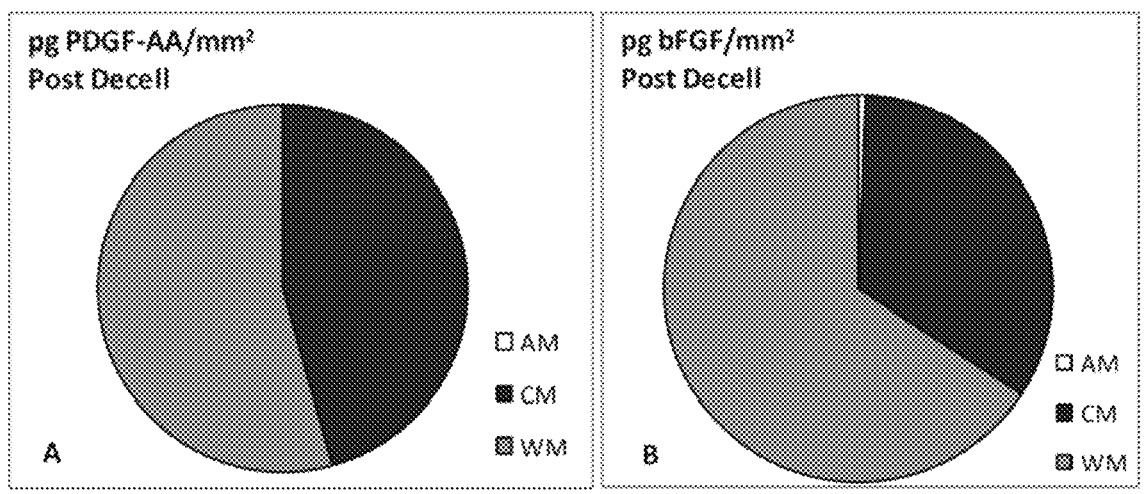
FIG. 10 depicts comparison of the quantity of PDGF-AA (A) and bFGF (B) in intact placental membrane (WM), isolated amniotic membrane (AM), and isolated chorionic membrane (CM) at the same size after decellularization. The quantity of PDGF-AA from the isolated amniotic membrane (AM) was below detection limit of the ELISA kit.

Growth factors in decellularized placental membrane: Representative samples from isolated amniotic membrane, isolated chorionic membrane, and intact placental membrane after cleaning and decellularization were cut to small pieces and incubated with HEPES buffer containing collagenase, hyaluronidase, protease inhibitors, and Triton X-100 for 20-24 hours at 37° C. with agitation. The resulting samples were sonicated briefly and followed by centrifugation at 10,000 g for 15 minutes at 4° C. The supernatant were aliquoted and used for growth factor quantification following instructions of ELISA kits for bFGF and PDGF-AA (Ray Biotech, Inc.). The bFGF and PDGF-AA results from 5 individual donors were measured and calculated. After decellularization, the total PDGF-AA from the intact placental membrane was about 18% more than the sum of PDGF-AA from isolated amniotic membrane and chorionic membrane at the same size (FIG. 10A). The total bFGF from the intact placental membrane was about 140% more than the sum of bFGF from isolated amniotic membrane and chorionic membrane at the same size (FIG. 10B). This suggests that the isolation of amniotic membrane and chorionic membrane can reduce the growth factor content compared to the intact placental membrane. The intact placental membrane with both amnion layer and chorion layer in contact can better maintain the bioactive factors than isolated amnion layer and chorion layer. Also our data showed the significantly high quantity of PDGF-AA and bFGF in chorionic membrane than amniotic membrane.

Example 8. Activity of Decellularized Intact Placental Membrane

Decellularized placental membrane pieces were prepared according to the processing steps described in Example 6. Representative samples were punched out of intact placental membrane after cleaning/decellularization steps and weighed aseptically. The intact placental membrane was extracted in Dulbecco's Modified Eagle Medium (DMEM) for 24 hours at 2 mg/mL with gentle agitation (75 RPM) at 37° C. A media control (only DMEM, without placental tissue) was also incubated alongside the placental membrane extractions. Media from 2 different groups were added to 48 well plates of human dermal fibroblast (HDF), seeded at 3500 cells/cm$^2$ the day before.

Figure 11:
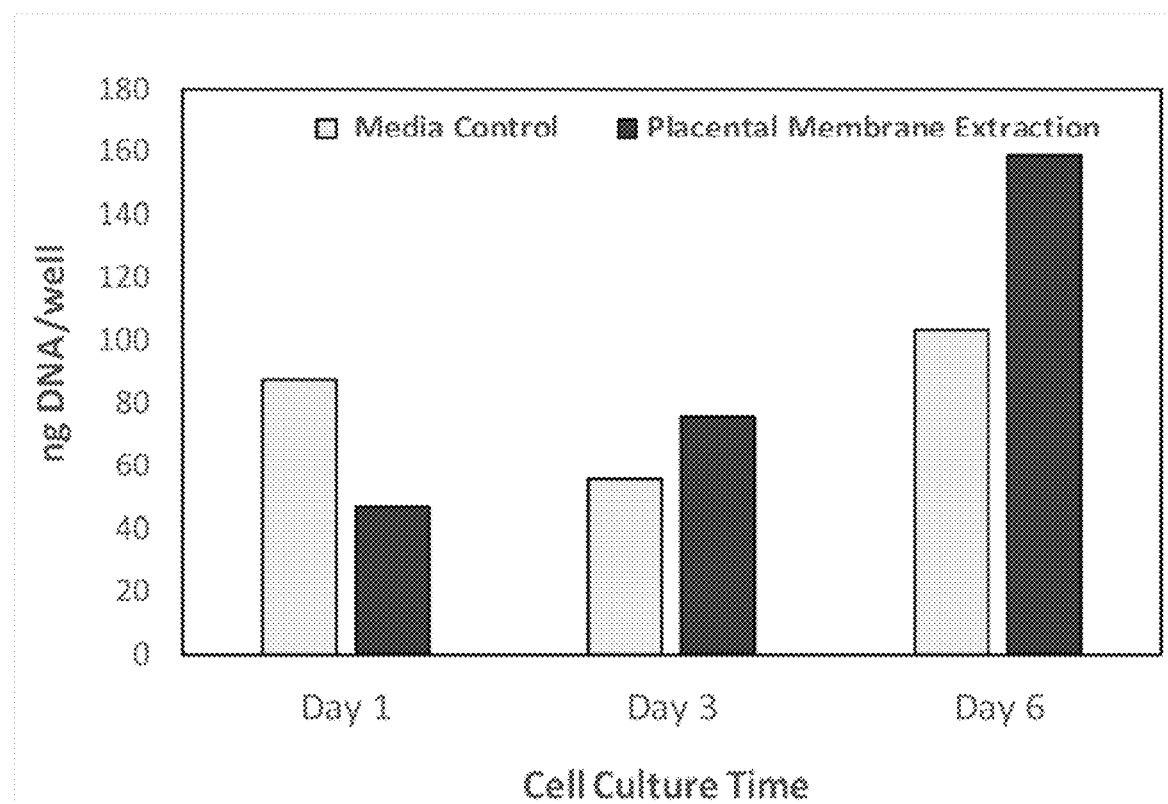
FIG. 11 depicts quantification of DNA in human dermal fibroblast (HDF) cells that were cultured in media control or media with a decellularized placental membrane extraction.

On days 1, 3, and 6, the cells were detached from the plate, centrifuged at 10000 RPM for 5 minutes, and the cell pellets were used for DNA quantification using PicoGreen DNA assay kit (Invitrogen Cat #P11496). The quantity of the total chromosomal DNA was used as the indication of the HDF cell number. The results showed that the HDF cell proliferation from day 1 through day 6 cultured with placental membrane extraction media (FIG. 11), and the percentage of DNA increased from day 1 to day 6 was 240%. The HDF cells cultured with control media alone did not show any significant proliferation over the same culture period, the percentage of DNA increased from day 1 to day 6 was about 18%.

The present invention is not limited to the embodiments described and exemplified above, but is capable of variation and modification within the scope and range of equivalents of the appended claims.

The invention claimed is:

1. A method of preparing a decellularized placental membrane, comprising
   (a) obtaining an amniotic sac cut from a placenta around a placenta skirt, wherein the amniotic sac comprises a pre-decellularized placental membrane and the pre-decellularized placental membrane comprises an amnion layer and a chorion layer,
   (b) treating the pre-decellularized placental membrane with one or more compounds selected from the group consisting of N-lauroylsarcosinate, n-octyl-b-D-glucopyranoside, a polyoxyethylene alcohol, a polyoxyethylene isoalcohol, a polyoxyethylene p-t-octyl phenol, a polyoxyethylene nonyphenol, a polyoxyethylene ester of a fatty acid, and a polyoxyethylene sorbitol ester, and
   (c) removing cells from the pre-decellularized placental membrane without separating the amnion layer from the chorion layer, wherein the cells comprise cells in the amnion layer and the chorion layer in the pre-decellularized placental membrane, whereby a decellularized placental membrane is prepared.

2. The method of claim 1, wherein the decellularized placental membrane comprises one or more growth factors in an amount that is at least 10% greater than the sum of the amount of the one or more growth factors in a decellularized control isolated amniotic membrane having the same size as the decellularized placental membrane and the amount of the one or more growth factors in a decellularized control isolated chorionic membrane having the same size as the decellularized placental membrane, wherein the decellularized control isolated amniotic membrane is prepared by removing cells from the amnion layer isolated from the pre-decellularized placental membrane in the same manner as the decellularized placental membrane is prepared from the pre-decellularized placental membrane, and wherein the decellularized control isolated chorion is prepared by removing cells from the chorion layer isolated from the pre-decellularized placental membrane in the same manner as the decellularized placental membrane is prepared from the pre-decellularized placental membrane.

3. The method of claim 1, wherein the decellularized placental membrane comprises one or more growth factors in an amount that is at least 20% of the amount of the one or more growth factors in the pre-decellularized placental membrane.

4. The method of claim 1, wherein the decellularized placental membrane comprises less than 100 ng dsDNA per mg dry weight of the decellularized placental membrane.

5. The method of claim 1, wherein the decellularized placental membrane comprises DNA in an amount that is less than 10% of the DNA in the pre-decellularized placental membrane.

6. The method of claim 1, wherein the amnion layer in the pre-decellularized placental membrane comprises a fibroblast layer, and wherein the chorion layer in the pre-decellularized placental membrane comprises a reticular layer.

7. The method of claim 1, wherein the amnion layer in the pre-decellularized placental membrane comprises epithelium, a basement membrane, a compact layer, a fibroblast layer, and a spongy layer, and wherein the chorion layer in the pre-decellularized placental membrane comprises a cellular layer, a reticular layer, a pseudo-basement membrane, and a trophoblast layer.

8. The method of claim 1, further comprising harvesting the amniotic sac from a donor.

9. The method of claim 1, further comprising cleaning and disinfecting the pre-decellularized placental membrane.

10. The method of claim 1, further comprising fixing the pre-decellularized placental membrane onto a frame before the cell removal step.

11. The method of claim 1, wherein the chorion layer in the pre-decellularized placental membrane comprises a trophoblast layer.

12. The method of claim 1, wherein the one or more compounds are present in the composition at a concentration of 0.01-5% (w/v).

13. The method of claim 1, further comprising treating the pre-decellularized placental membrane with one or more endonucleases at a concentration of 20-400 U/mL.

14. A decellularized placental membrane prepared by the method of claim 1.

15. A placenta-derived graft comprising the decellularized placental membrane of claim 14 and one or more agents.

16. A method comprising culturing cells in the presence of the decellularized placental membrane prepared by the method of claim 1.

17. A method of promoting differentiation of pluripotent stem cells or tissue-specific progenitor cells, comprising culturing the pluripotent stem cells or tissue-specific progenitor cells in the presence of an effective amount of the decellularized placental membrane prepared by the method of claim 1.

18. A method of repairing a defect in a tissue, comprising contacting the site of the defect with an effective amount of the decellularized placental membrane prepared by the method of claim 1.

* * * * *